United States Patent
Gondry et al.

(10) Patent No.: US 7,112,425 B2
(45) Date of Patent: Sep. 26, 2006

(54) POLYNUCLEOTIDES AND POLYPEPTIDES CODED BY SAID POLYNUCLEOTIDES INVOLVED IN THE SYNTHESIS OF DIKETOPIPERAZINE DERIVATIVES

(75) Inventors: Muriel Gondry, Limours-en-Hurepoix (FR); Roger Genet, Limours-en-Hurepoix (FR); Sylvie Lautru, Verneuil-sur-Seine (FR); Jean-Luc Pernodet, Cachan (FR)

(73) Assignees: Commissariat A L'Energie Atomique, Paris (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 10/518,019

(22) PCT Filed: Jun. 18, 2003

(86) PCT No.: PCT/FR03/01851

§ 371 (c)(1),
(2), (4) Date: Apr. 13, 2005

(87) PCT Pub. No.: WO04/000879

PCT Pub. Date: Dec. 31, 2003

(65) Prior Publication Data

US 2006/0051837 A1    Mar. 9, 2006

(30) Foreign Application Priority Data

Jun. 21, 2002   (FR) ................... 02 07728

(51) Int. Cl.
| | |
|---|---|
| C12P 21/04 | (2006.01) |
| C12N 1/15 | (2006.01) |
| C12N 1/21 | (2006.01) |
| C12N 9/80 | (2006.01) |
| C12N 9/00 | (2006.01) |
| C12N 5/10 | (2006.01) |
| C07H 21/04 | (2006.01) |

(52) U.S. Cl. ............ 435/183; 435/252.33; 435/252.35; 435/228; 435/320.1; 435/252.3; 435/325; 536/23.2

(58) Field of Classification Search ............... 435/69.1, 435/252.33, 252.35, 228, 183, 320.1, 252.3, 435/325; 536/23.2
See application file for complete search history.

(56) References Cited

OTHER PUBLICATIONS

GenBank Accession No. AY129235, *Streptomyces noursei* putative tRNA (5-methylaminomethyl-2-thiouridylate)-methyltransferase gene, partial cds; albonoursin biosynthetic gene cluster, complete sequence; and putative NADP-specific glutamate dehydrogenase gene.*

Gondry, M. et al. "Cyclic dipeptide oxidase from *Streptomyces noursei* Ioslation, purification and partial characterization of a novel, amino acyl α, β-dehydrogenase", *Eur. J. Biochem.*, vol. 268 pp. 1712-1721, 2001.

Kanzaki, H. et al. "Enzymatic Conversion of Cyclic Dipeptides to Dehydro Derivatives that Inhibit Cell Division", *Journal of Bioscience and Bioengineering*, vol. 90(1) pp. 86-89, 2000.

Kanzaki, H. et al. "Biosynthetic Intermediates of the Tetradehydro Cyclic Dipeptide Albonoursin Produced by *Streptomyces albulus* KO-23", *The Journal of Antibiotics*, vol. 53 (11) pp. 1257-1264, 2000.

Lautru, S. et al. "The Albonoursin Gene Cluster of *S. noursei*: Biosynthesis of Diketopiperazine Metabolites Independent of Nonribosomal Peptide Synthetases", *Chemistry & Biology*, vol. 9 pp. 1355-1364, 2002.

* cited by examiner

*Primary Examiner*—Rebecca E. Prouty
*Assistant Examiner*—Iqbal Chowdhury
(74) *Attorney, Agent, or Firm*—Nath & Associates PLLC; Gary M. Nath; Tanya E. Harkins

(57) ABSTRACT

The invention concerns novel isolated natural or synthetic polynucleotides and polypeptides coded by said polynucleotides, involved in the synthesis of diketopiperazine derivatives, vectors comprising said polynucleotides, micro-organisms transformed with said polynucleotides, uses of said polynucleotides and said polypeptides, as well as methods for the synthesis of diketopiperazine derivatives, including cyclodipeptides and diketopiperazine derivatives 3- and 6-substituted by α,β-unsaturated amino acid side chains.

12 Claims, 7 Drawing Sheets

In *Escherichia coli* pSL122
pSL127
pSL145

In *Streptomyces lividans* pSL 142
pSL 168
pSL 159
pSL 167
pSL 128

POLYNUCLEOTIDES AND POLYPEPTIDES CODED BY SAID POLYNUCLEOTIDES INVOLVED IN THE SYNTHESIS OF DIKETOPIPERAZINE DERIVATIVES

The present invention relates to novel isolated, natural or synthetic polynucleotides and to the polypeptides encoded by said polynucleotides, that are involved in the synthesis of diketopiperazine derivatives, to the vectors comprising said polynucleotides, to the microorganisms transformed with said polynucleotides, to the applications of said polynucleotides and of said polypeptides, and also to processes for synthesizing diketopiperazine derivatives, including cyclodipeptides and diketopiperazine derivatives substituted in the 3- and 6-positions with α,β-unsaturated amino acid side chains.

For the purposes of the present invention, the term "diketopiperazine derivatives" is intended to mean molecules having a diketopiperazine ring (piperazine-2,5-diones or 2,5-dioxopiperazines or 2,5-DKP), substituted in the 3- and the 6-positions with amino acids. In the particular case of cyclic diamino acids (cyclodipeptides or cyclic dipeptides), the substituent groups in the 3- and 6-positions are the amino acid side chains. In the particular case of bisdehydro cyclic diamino acids (bisdehydro cyclic dipeptides), the substituent groups in the 3- and 6-positions are α,β-unsaturated amino acid side chains (FIG. 1).

Diketopiperazine derivatives constitute a family of compounds essentially produced by microorganisms such as bacteria, yeast, filamentous fungi and lichens. Others have also been isolated from marine organisms, such as sponges and starfish. An example of these derivatives has been demonstrated in humans: cyclo(L-His-L-Pro).

The diketopiperazine derivatives have very varied structures ranging from simple cyclodipeptides to much more complex structures.

The simple cyclodipeptides constitute only a small fraction of the diketopiperazine derivatives, the majority of which have more complex structures in which the main ring and/or the side chains comprise many modifications: introduction of carbon-based, hydroxyl, nitro, epoxy, acetyl or methoxy groups, and also the formation of disulfide bridges or of heterocycles. The formation of a double bond between two carbons is also quite widespread. Certain derivatives, of marine origin, incorporate halogen atoms.

Some examples of amino acids incorporated into the cyclodipeptides are given in table I below:

TABLE 1

| Cyclodipeptide | Organism |
| --- | --- |
| Cyclo(Gly-L-Pro) | Luidia clathrata |
| Cyclo(L-Pro-L-Leu) | Rosellinia necatrix |
| Cyclo(L-Ala-L-Val) | Aspergillus ochraceus |
| Cyclo(L-Ala-L-Leu) | Aspergillus niger |
| Cyclo(D-Ala-N-méthyl-L-Leu) | Beauveria nivea |
| Cyclo(L-Pro-L-Val) | Aspergillus ochraceus |
| Cyclo(L-Pro-L-Leu) | Rosellinia necatrix |
| Cyclo(D-Val-L-Trp) | Aspergillus chevalieri |
| Cyclo(L-Phe-L-Phe) | Penicillium nigricans Streptomyces noursei |
| Cyclo(ΔPhe-ΔLeu) (albonoursin) | Streptomyces noursei |
| Cyclo(L-Pro-L-Tyr) | Alternaria alternata |
| Cyclo(L-Pro-L-Trp) | Penicillium brevicompactum |
| Cyclo(L-Ser-L-Ser) | Streptomyces orchidaceus |
| Cyclo(L-Arg-D-Pro) | Pseudomonas sp. |
| Phenylhistine Roquefortine | Penicillium roquefortii |

TABLE 1-continued

| Cyclodipeptide | Organism |
| --- | --- |
| Cyclo(L-Trp-ΔAba) | Streptomyces spectabilis |
| Cyclo(4-methyl-D-Pro-L-Nva) | Calyx cf. podatypa |
| Cyclo(ΔAla-L-Val) | Pseudomonas aeruginosa |

Very little is known regarding the physiological role of diketopiperazine derivatives. It has been described that the cyclo(ΔAla-L-Val) produced by *Pseudomonas aeruginosa* could be involved in interbacterial communication signals. Other compounds are described as being involved in the virulence of pathogenic microorganisms or else as binding to iron or as having neurobiological properties.

The diketopiperazine derivatives have proved to be advantageous since the discovery that some of them have biological properties such as, for example, antibacterial, antifungal, antiviral, immunosuppressive or antitumor activities.

Table II below gives some examples of diketopiperazine derivatives having a known biological activity:

TABLE II

| Molecules | Organism | Activity |
| --- | --- | --- |
| Ambewelamides A and B | Usnea sp. | Cytotoxicity |
| Aranotin | Arachniotus aureus | Antiviral |
| Bicyclomycin | Streptomyces sapporonensis | Antibacterial (inhibition of transcription termination) |
| Cyclo(Δ-Ala-L-Leu) | Penicillium sp. (F70614) | Inhibition of α-glucosidase |
| Cyclo(N-methyl-Tyr)₂ | Streptomyces griseus | Inhibition of calpain |
| Cyclo(Trp-Δ-Aba) | Streptomyces spectabilis | Inhibition of glutathione-S-transferase |
| Gliotoxin | Aspergillus flavus | Herbicidal, antifungal, antibacterial, antiviral |
| Haematocin | Nectria haematococca | Antifungal |
| Hyalodendrin | Penicillium turbatum | Antibiotic |
| Mycelianamide | Penicillium sp. | Antibacterial (inhibition of butylcholinesterase) |
| Phenylhistine | Aspergillus ustus (NSC-FO38) | Inhibition of microtubule polymerization |
| Tan-1496 A, C and E | Microphaeropsis sp. (FL-16144) | Inhibition of topoisomerase Antibacterial (Gram+) |
| Verticillin A | Gliocladium sp. (SCF-1168) | Inhibition of induction of the c-fos protooncogene |
| XR334 | Streptomyces sp. (X01/4/100) | Inhibition of PAI-I |

Although the study of these molecules has become widely developed, little is known regarding their synthesis. It is generally known that, in bacteria and in fungi, these molecules are produced by non-ribosomal biosynthesis. In certain cases, it has been possible to show that the formation of the diketopiperazine ring occurs in molecules which are pre-activated via a thioester bond with an enzyme and for which the cis-conformation of the peptide bond, which is necessary for the cyclization reaction, is promoted by the presence of proline residues. In other cases, it has been demonstrated that N-alkylation, particularly N-methylation, of the amino acid residues also promotes the cis-conformation of the peptide bond.

Thus, all these studies carried out to date have demonstrated that the primary structure of the precursor molecule, which conditions its conformation, is fundamental for the formation of the diketopiperazine ring to take place and for the process to result in the production of the final diketopiperazine derivative.

However, diketopiperazine derivatives exist which do not contain a proline residue or an N-alkylated residue. By way of example of such derivatives, mention may be made of albonoursin, or cyclo(ΔPhe-ΔLeu), an antibiotic produced by *Streptomyces noursei*. It is known that there exists in *Streptomyces noursei* an enzyme activity which catalyzes the final step of the production of albonoursin, namely the formation of the α,β-unsaturated residues (Gondry et al., Eur. J. Biochem., 2001, 268, 1712–1721). However, this enzyme activity requires a substrate in cyclic form, cyclo [L-Phe-L-Leu], which does not contain a proline residue or any N-alkylated residue, and for which the synthetic pathway is unknown.

Thus, the diketopiperazine derivatives exhibit a very great structural diversity and very varied biological activities which make them advantageous molecules for discovering and developing novel medicinal products.

To do this, it is necessary to be able to have large amounts of these molecules.

Admittedly, pathways for the chemical synthesis of diketopiperazine derivatives have been described, but for the most complex derivatives, the yields are low and the processes can not always be industrialized.

An understanding of the pathways for the natural synthesis of the diketopiperazine derivatives, particularly that of cyclodipeptides, could enable a reasoned genetic improvement in the producer organisms, and would open up perspectives for substituting or improving the existing processes for synthesis (via chemical or biotechnological pathways) through the optimization of production and purification yields. In addition, modification of the nature and/or of the specificity of the enzymes involved in the biosynthetic pathway for the diketopiperazine derivatives could result in the creation of novel derivatives with original molecular structures and with optimized biological properties.

The present invention falls within this context.

In studying the synthetic pathway for albonoursin, the inventors have demonstrated a polynucleotide (hereinafter referred to as BamH1 polynucleotide (SEQ ID No.5)), comprising four open reading frames, each one encoding a polypeptide responsible for each one of the steps for the synthesis and for the transport of albonoursin, from L-phenyl-alanine and L-leucine residues, in *Streptomyces noursei* and in heterologous hosts such as *Streptomyces lividans* (see FIGS. 2 and 3).

The inventors have been able to show that:
the first open reading frame orf1 (albA, SEQ ID No.1) encodes a polypeptide (AlbA, SEQ ID No.6) involved in a cyclodipeptide oxidase (CDO) activity such as that described in Gondry et al., (Eur. J. Biochem., 2001, 268, 1712–1721 (α,β-desaturation);
the second open reading frame orf2 (albB, SEQ ID No.2) encodes a polypeptide which is translated as two isoforms (AlbB$_2$, SEQ ID No.7 and AlbB$_2$, SEQ ID No.8) required for the activity of the AlbA polypeptide. The two isoforms of AlbB which are expressed in more or less equivalent amounts differ from one another by virtue of the presence of 5 additional amino acids located at the N-terminal end of AlbB$_1$ and resulting from the use of two different initiation codons. In the case of AlbB$_1$, the initial methionine is eliminated;

the third open reading frame orf3 (albC, SEQ ID No.3) encodes a polypeptide (AlbC, SEQ ID No.9) which shows no similarity with a peptide synthetase and which is capable of catalyzing the condensation of two amino acid residues so as to form a cyclic dipeptide. For example in *Streptomyces noursei*, AlbC catalyzes the condensation of an L-phenylalanine and of an L-leucine or of two L-phenylalanines, so as to form the cyclic dipeptide cyclo(L-Phe-L-Leu), which is a precursor required for the formation of albonoursin and the cyclic dipeptide cyclo(L-Phe-L-Phe). In this particular case, AlbC catalyzes the cyclization of amino acid residues which are neither a proline nor an N-alkylated residue, and the fourth open reading frame orf4 (albD, SEQ ID No.4) encodes a polypeptide (AlbD, SEQ ID No.10) which is not directly involved in the succession of reactions resulting in the formation of α,β-unsaturated diketopiperazine derivatives from amino acids, but is probably involved in the mechanism of transport of said derivatives.

The inventors have thus shown that, for the synthesis of α,β-unsaturated diketopiperazine derivatives, only the three open reading frames albA, albB and albC are absolutely necessary, particularly for the synthesis of albonoursin in *Streptomyces noursei*.

Thus, a subject of the invention is an isolated, natural or synthetic polynucleotide characterized in that it comprises at least the three open reading frames albA, albB and albC corresponding, respectively, to the sequences SEQ ID No.1, SEQ ID No.2 and SEQ ID No.3.

This polynucleotide encodes the enzymes required for the synthesis of α,β-unsaturated diketopiperazine derivatives.

According to an advantageous embodiment of the invention, said polynucleotide also comprises the open reading frame albD corresponding to the sequence SEQ ID No.4.

This polynucleotide encodes the enzymes required for the synthesis of α,β-unsaturated diketopiperazine derivatives and for their transport and for their secretion.

According to a particular form of the invention, the polynucleotide corresponds to the sequence SEQ ID No.5. This polynucleotide (BamH1 polynucleotide) contains the four open reading frames albA, albB, albC and albD, and therefore encodes the enzymes required for the synthesis of α,β-unsaturated diketopiperazine derivatives and for their transport and for their secretion.

A subject of the invention is also an isolated, natural or synthetic polynucleotide characterized in that it comprises at least one of the three open reading frames albB, albC and albD corresponding, respectively, to the sequences SEQ ID No.2, SEQ ID No.3 and SEQ ID No.4.

Thus, the polynucleotide comprising the open reading frame albC (SEQ ID No.3) encodes an enzyme which allows the cyclization of two amino acids, which may be identical or different, so as to form a cyclic dipeptide. The polynucleotide comprising the open reading frames albC and albD (SEQ ID No.3 and SEQ ID No.4) encodes the enzymes which allow, firstly, the cyclization of two amino acids, which may be identical or different, so as to form a cyclic dipeptide and, secondly, the transport of said dipeptide.

The subject of the invention is also an isolated, natural or synthetic polynucleotide corresponding to any one of the sequences SEQ ID No.2 (albB, 318 nucleotides), SEQ ID No.3 (albC, 720 nucleotides) or SEQ ID No.4 (albD, 834 nucleotides).

A subject of the invention is also fragments of the polynucleotides as defined above. The term "fragment" is intended to mean any sequence of at least 15 nucleic acids.

The polynucleotide according to the invention can be obtained from DNA libraries, particularly from microorganism DNA libraries, very particularly from a *Streptomyces noursei* DNA library. The polynucleotide of the invention can also be obtained by means of a polymerase chain reaction (PCR) carried out on the total DNA of *Streptomyces noursei*. The polynucleotides according to the invention can be obtained by RT-PCR carried out on the total RNA of *Streptomyces noursei*.

A subject of the invention is also a vector into which is inserted any one of the polynucleotides described above. Thus, the vector of the invention can comprise the polynucleotide comprising the three or the four open reading frames albA, albB, albC and/or albD, corresponding, respectively, to the sequences SEQ ID No.1, SEQ ID No.2, SEQ ID No.3 and/or SEQ ID No.4, the polynucleotide comprising at least one of the three open reading frames albB, albC or albD corresponding, respectively, to the sequences SEQ ID No.2, SEQ ID No.3 and SEQ ID No.4, any one of the polynucleotides corresponding to at least one of the three open reading frames albB, albC or albD corresponding, respectively, to the sequences SEQ ID No.2, SEQ ID No.3 and SEQ ID No.4, the BamH1 polynucleotide corresponding to the sequence SEQ ID No.5 or else a fragment of said polynucleotides.

The vector used may be any known vector of the prior art. As vectors that can be used according to the invention, mention may in particular be made of plasmids, cosmids, bacterial artificial chromosomes (BACs), integrative elements of actinobacteria, viruses or else bacteriophages.

Said vector may also comprise any regulatory sequences required for the replication of the vector and/or the expression of the polypeptide encoded by the polynucleotide (promoter, termination sites, etc.).

A subject of the invention is also the use of at least one of the polypeptides as defined above, or of one of its fragments, as a probe for detecting corresponding sequences in other organisms or as a primer for amplifying such sequences.

When they are primers, said polynucleotides or said fragments also include antisense sequences.

One of the preferred uses of the probes or primers described above is the investigation of polynucleotide sequences homologous to the sequences of the open reading frames albA, albB, albC or albD in other organisms, in order in particular to demonstrate novel synthetic pathways for diketopiperazine derivatives.

A subject of the invention is also an isolated, natural or synthetic polypeptide characterized in that it comprises at least any one of the sequences SEQ ID No.7 to SEQ ID No.10, corresponding, respectively, to the polypeptides $AlbB_1$, $AlbB_2$, AlbC or AlbD.

A subject of the invention is also an isolated, natural or synthetic polypeptide characterized in that it corresponds to any one of the sequences SEQ ID No.7 ($AlbB_1$), SEQ ID No.8 ($AlbB_2$), SEQ ID No.9 (AlbC) or SEQ ID No.10 (AlbD).

The invention also relates to the polypeptides encoded by any one of the polynucleotides of the invention, particularly any one of the polynucleotides chosen from any one of the sequences SEQ ID No.2 (albB), SEQ ID No.3 (albC) or SEQ ID No.4 (albD).

Advantageously, the polypeptides according to the invention can be either isolated from microorganisms (*Streptomyces noursei*) for example, or obtained by chemical synthesis or else by biotechnological means, from the polynucleotides of the invention, such as, for example, from modified microorganisms which do not normally express said polypeptides.

A subject of the invention is also an isolated polypeptide, the sequence of which is substantially homologous to at least one of the sequences SEQ ID No.7 to SEQ ID No.10, as defined above.

It is considered here that a polypeptide has a substantially homologous sequence when its amino acid sequence exhibits at least 80% similarity with the amino acid sequence of at least one of the sequences SEQ ID No.7 to SEQ ID No.10 and when the polypeptide has conserved its initial activity.

The expression "80% similarity between a polypeptide P and the sequences SEQ ID No. 7 to 10" is intended to mean that, when the two polypeptides are aligned, 80% of the amino acids of P are identical to the corresponding amino acid of the sequences SEQ ID No.7 to 10 or are replaced with an amino acid of the same group.

The expression "amino acid of the same group" is intended to mean an amino acid having substantially identical chemical properties. In particular, this term is intended to mean amino acids having substantially the same charge and/or the same size and/or the same hydrophilicity or hydrophobicity and/or the same aromaticity.

Such amino acid groups include in particular:
(i) glycine, alanine
(ii) isoleucine, leucine, valine
(iii) tryptophan, tyrosine, phenylalanine
(iv) aspartic acid, glutamic acid
(v) arginine, lysine, histidine
(vi) serine, threonine.

Other substitutions can be envisioned, in which an amino acid is replaced with another amino acid that is comparable but not natural (hydroxyproline, norleucine, ornithine, citrulline, cyclohexylalanine, dextrorotatory amino acids, etc.).

A subject of the invention is also the use of the polynucleotides or the vectors of the invention as described above, for synthesizing polypeptides corresponding to the sequences SEQ ID Nos.7 to 10.

A subject of the invention is also the use, particularly in vitro, of the polypeptides according to the invention, alone or in combination, for preparing cyclodipeptides and/or diketopiperazine derivatives substituted in the 3- and 6-positions with α,β-unsaturated amino acid side chains, particularly albonoursin.

A subject of the invention is also the use of the polypeptides of the invention, alone or in combination, for modifying the pharmacological activity of a biological molecule by modifying its structure, for example by dehydrogenation of side chains, particularly of amino acid side chains, or by cyclization, particularly of peptide molecules.

A subject of the invention is also a modified biological system into which at least one polynucleotide according to the invention or at least one vector according to the invention has been introduced.

Such a biological system may be any known heterologous expression system using prokaryotes or eukaryotes as hosts. By way of example, mention may be made of a microorganism, for instance a bacterium such as *Escherichia coli* or *Streptomyces lividans*, or animal or insect cells.

A subject of the invention is also a modified in vitro acellular system into which at least one polynucleotide according to the invention or at least one vector according to the invention has been introduced.

A subject of the invention is also the use of at least one polynucleotide according to the invention and/or of at least one vector according to the invention, for preparing a modified biological system, it being possible for said system to be a microorganism, for instance a bacterium such as *Escherichia coli* or *Streptomyces lividans*, or any known heterologous expression system using prokaryotes or eukaryotes as hosts, or else a modified in vitro acellular system.

The introduction of the polynucleotide and/or of the vector according to the invention into the host modified biological system can be carried out by any known method, such as, for example, transfection, infection, fusion, electroporation, microinjection or else biolistics.

A subject of the invention is also the use of at least one modified biological system or of at least one modified in vitro acellular system, as defined above, for preparing cyclodipeptides and/or diketopiperazine derivatives substituted in the 3- and 6-positions with α,β-unsaturated amino acid side chains, particularly albonoursin.

The biological systems are suitable for the synthesis, with a good yield, of the cyclodipeptides and of the α,β-unsaturated diketopiperazine derivatives as defined above.

When it is a microorganism, the modified biological system may also optionally allow the secretion of the diketopiperazine derivative according to the invention into a culture medium, making it easier to extract it and purify it. The presence of AlbD in the biological systems such as microorganisms constitutes an advantageous step for the industrial process by facilitating the extraction and purification of the derivative, which is thus secreted into the culture medium.

A subject of the invention is also a method for the in vitro synthesis of a cyclodipeptide, characterized in that:

(1) two amino acids, which may be identical or different, are brought into contact, under suitable conditions, with AlbC (SEQ ID No.9) and (2) the cyclodipeptide obtained is purified.

A subject of the invention is also a method for the in vitro synthesis of a diketopiperazine derivative substituted in the 3- and 6-positions with α,β-unsaturated amino acid side chains, characterized in that:

(1) two amino acids, which may be identical or different, are brought into contact, under suitable conditions, with AlbC (SEQ ID No.9) and (2) the cyclodipeptide obtained in step (1) is brought into contact with AlbA (SEQ ID No.6), AlbB1 (SEQ ID No.7) and AlbB2 (SEQ ID No.8), and then the α,β-unsaturated diketopiperazine derivative obtained is purified. The method may also include, in step (2), the polypeptide AlbD (SEQ ID No.10). The method may optionally comprise, between step (1) and step (2), an additional step for purification of the cyclodipeptide obtained in step (1).

This method can, of course, be carried out in a single step in which two amino acids, which may be identical or different, are brought into contact, under suitable conditions, with AlbA (SEQ ID No.6), AlbB1 (SEQ ID No.7), AlbB2 (SEQ ID No.8) and AlbC (SEQ ID No. 9), optionally AlbD (SEQ ID No.10), and the α,β-unsaturated diketopiperazine derivative obtained is purified.

The term "suitable conditions" is preferably intended to mean the conditions under which the following are incubated:

the polypeptides (AlbA, AlbB, AlbC and/or AlbD) at concentrations of between 0.1 nM and 10 μM, preferably of between 10 nM and 1 μM;

in the presence of amino acids, which may be identical or different, at a concentration of between 0.1 mM and 100 mM, preferably of between 1 mM and 10 mM;

in a 0.1 M Tris-HCl buffer, having a pH of between 6.8 and 8.0, at a temperature of between 28° C. and 40° C., for a period of time of between 2 hours and 48 hours.

A subject of the invention is also a method for synthesizing a cyclodipeptide, characterized in that:

(1) a biological system comprising at least the polynucleotide SEQ ID No.3 (albC, encoding AlbC) is brought into contact, under conditions suitable for culturing said chosen biological system, and (2) the cyclodipeptide obtained is purified. The biological system may also comprise the polynucleotide SEQ ID No.4 (encoding AlbD).

A subject of the invention is also a method for synthesizing a diketopiperazine derivative substituted in the 3- and 6-positions with α,β-unsaturated amino acid side chains, characterized in that:

(1) a biological system comprising the polynucleotide corresponding to the sequences SEQ ID Nos.1 to 3 (encoding AlbA, AlbB, and AlbC) is brought into contact, under conditions suitable for culturing said chosen biological system, and (2) the α,β-unsaturated diketopiperazine derivative obtained is purified. The biological system may also comprise the polynucleotide corresponding to the sequence SEQ ID No.4 (encoding AlbD).

The expression "conditions suitable for culturing said chosen biological system" is understood to mean that the method is carried out under the conditions for culturing the chosen biological system, including a suitable culture medium containing a large excess of amino acids. For example, if the biological system is a microorganism, such as, for example, *Escherichia coli*, the suitable conditions are those commonly used for culturing this bacterium. The same is true for *Streptomyces lividans* or if the biological system is a eukaryotic cell.

According to the methods of the invention, the amino acids, which may be identical or different, are present in an amount of between 0.1 mM and 100 mM, preferably of between 1 mM and 10 mM.

Similarly, according to the methods of the invention, the polypeptides AlbA, AlbB, AlbC and AlbD are present in an amount of between 0.1 nM and 10 μM, preferably of between 10 nM and 1 μM.

The purification of the cyclodipeptides and of the α,β-unsaturated diketopiperazine derivatives can be carried out directly from syntheses in vivo or in vitro by means of liquid-phase extraction techniques or by means of precipitation, or thin-layer or liquid-phase chromatography techniques, in particular reverse-phase HPLC, or any method suitable for purifying peptides, one known to those skilled in the art.

The methods of the invention may be carried out in any suitable biological system, particularly in a host such as, for example, a microorganism, for instance a bacterium such as *Escherichia coli* or *Streptomyces lividans*, or any known heterologous expression system using prokaryotes or eukaryotes as hosts, or even in vitro acellular systems.

Besides the above provisions, the invention also comprises other provisions which would emerge from the following description, which refers to examples of implementation of the invention and also to the attached drawings, in which.

A: *S. lividans*[pSL168], incubated in the presence of CDO;

B: *S. lividans*[pSL168], incubated in the absence of CDO;

C: *S. lividans*[pSL159] in the absence or in the presence of CDO;

D: *Streptomyces lividans* TK21 incubated in the presence of CDO.

Figure 7:
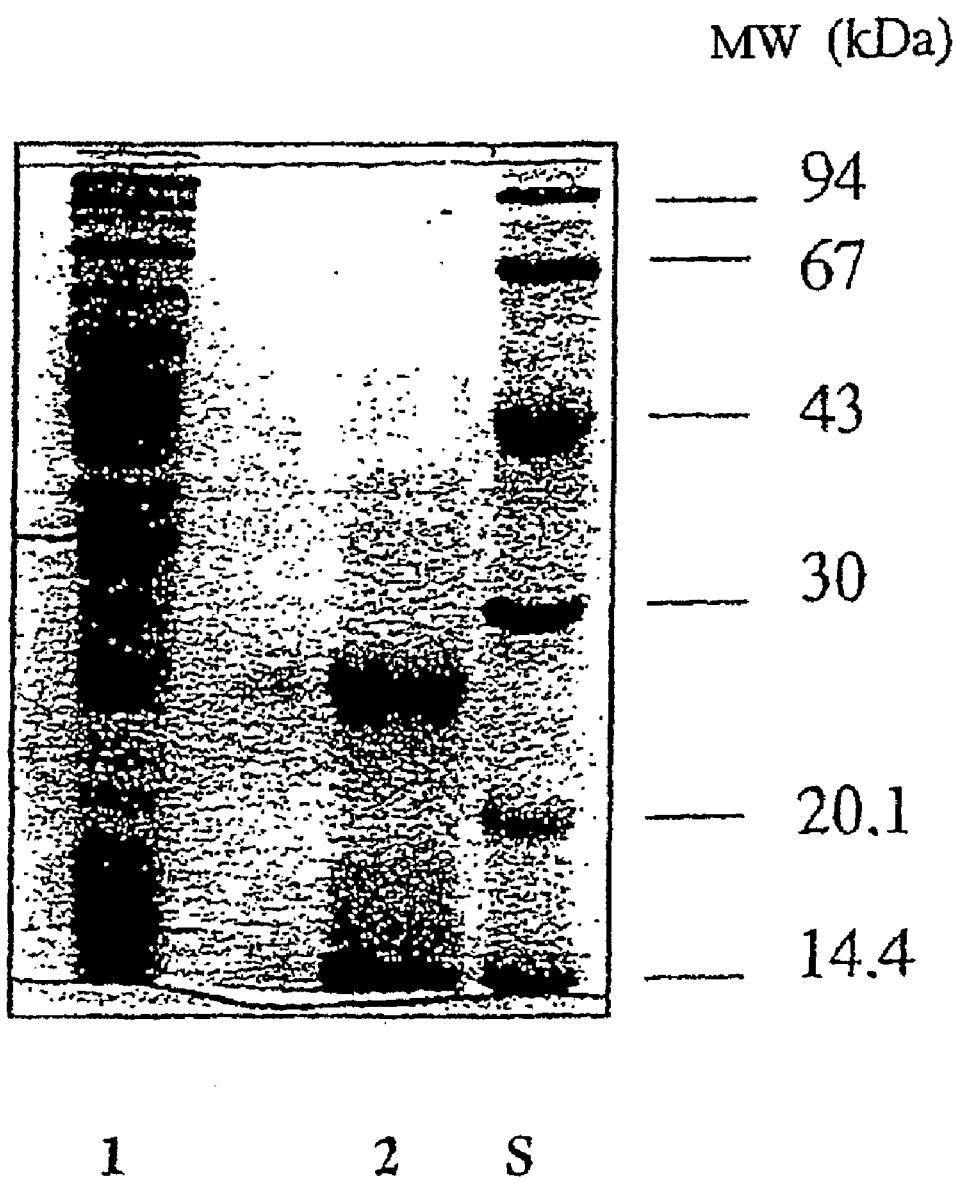

FIG. 7 represents the sodium dodecyl sulfate/polyacrylamide gel (SDS-PAGE) analysis of the expression of AlbA and AlbB$_1$ and AlbB$_2$ from the polynucleotide albA–albB in *E. coli* BL21(DE3)-plysS. Staining with Coomassie brilliant blue R-250. Lane S: molecular weight standard, lane 1: total cytoplasmic extract (approximately 10 μg), lane 2: enzyme fraction purified on an Ni-sepharose column (approximately 10 μg).

The following examples illustrate the invention but in no way limit it.

EXAMPLE 1

Isolation of the Polynucleotide of the Invention in *Streptomyces noursei*

A polynucleotide containing all the genetic information required for the biosynthesis of albonoursin in *Streptomyces noursei* was isolated from the total genome of this microorganism by an approach based on gene amplification by PCR.

Obtaining partial peptide sequences of the cyclodipeptide oxidase:

Partial peptide sequence information on the enzyme which catalyzes, in *Streptomyces noursei*, the conversion of the cyclodipeptide cyclo(L-Phe-L-Leu) to albonoursin, called cyclodipeptide oxidase (CDO), was obtained by direct sequencing, by the Edman method, of polypeptides derived from trypsin hydrolysis of the purified enzyme according to the protocol described in M. Gondry et al. (Gondry et al., 2001, mentioned above). After separation of the enzyme fraction constituents by 15% polyacrylamide gel electrophoresis and staining of the proteins with Coomassie blue, a gel band containing the protein of molecular mass of approximately 21000 daltons is cut out and incubated in 1 ml of 50 mM Tris-HCl buffer, pH 8, in the presence of trypsin (relative trypsin/substrate concentrations=1/50), for 20 hours at 37° C. The polypeptides obtained are then separated by reverse-phase high performance liquid chromatography (HPLC) (μRPC C$_2$/C$_{18}$ SC21/10 column, Pharmacia) with a linear gradient of 0% to 76% of acetonitrile in 62 minutes (solvent: 0.1% trifluoroacetic acid; flow rate: 1 ml/min). Each of the separated polypeptides is then purified by gel permeation chromatography on a superdex peptide PC32/30 column (Pharmacia) equilibrated in buffer containing 30% of acetonitrile and 0.1% of trifluoroacetic acid. Three of the polypeptides obtained were finally analyzed by automatic sequencing by the Edman method (model 477A sequencer, Applied Biosystems) and by MALDI-TOF mass spectrometry. Table 1 gives the peptide sequences obtained and also the nucleotide sequences which were deduced therefrom.

TABLE I

| Peptide sequence | Deduced nucleotide sequence |
|---|---|
| (SEQ ID N°11) EPVDDALIEQLLEAMLAAPT | (SEQ ID N°14) GARCCSGTSGACGACGC (oligo1f) |
| | (SEQ ID N°15) GCGTCGTCSACSGGYTC (oligo1r) |
| (SEQ ID N°12) NEVVNYEXWGNR | (SEQ ID N°16) AACGARGTSGTSAACTACGA (oligo2f) |
| | (SEQ ID N°17) TCGTAGTTSAOSACYTCGTT (oligo2r) |
| (SEQ ID N°13) QAXSFMVVR | (SEQ ID N°18) CAGGCSTGGWSSTTCATGGT (oligo3f) |
| | (SEQ ID N°19) ACCATGAASSWCCASGCCTG (oligo3r) |

X: undetermined amino acid (R=A or G; S=C or G; Y=C or T and W=A or T).

Comparison of the experimental and theoretical masses of the polypeptide corresponding to the sequence SEQ ID No.13 makes it possible to identify a tryptophan residue in the 3-position. The sequences underlined and in bold were used to design 6 sense (1f, 2f and 3f) and antisense (1r, 2r and 3r) degenerate oligonucleotides, according to the typical codon use in *Streptomyces*. In the absence of the information regarding the respective position of the polypeptides in the protein sequence, a combination of the six oligonucleotides was used for the cloning. Since the PCR conditions tested resulted in too great a number of amplified nucleotide fragments, a reverse transcription (RT-PCR) strategy was developed.

Amplification of an oligonucleotide fragment by RT-PCR:

The total RNA of *Streptomyces noursei* was extracted from a 24-hours culture in medium 5 (ATCC medium) according to the protocol described by Kieser et al. (Practical *Streptomyces* Genetics. The John Innes Foundation Norwich, U.K. (2000)). An additional treatment with DNase I makes it possible to completely eliminate the DNA. The degenerate oligonucleotides (sense and antisense) were synthesized by Sigma Genosys Ltd and the RT-PCR was carried out using the Titan™ One Tube RT-PCR kit (Boehringer Mannheim) according to the standard instructions, with 1 μg of total RNA for each reaction. The reverse transcription is carried out at 50° C. for 30 minutes, and the PCR conditions are then as follows: initial denaturation at 97° C. for 4 min, followed by 45 cycles of 1 min at 95° C., 1 min at 50° C. and 1 min at 68° C., and the final polymerization reaction at 68° C. for 10 minutes. The reaction products are analyzed by 1.5% agarose gel electrophoresis, and then purified (DNA and Gel Band purification kit, Pharmacia).

The RT-PCR with the six oligonucleotide combinations resulted in the amplification of a single fragment of approximately 400 base pairs, with the oligonucleotides 3f and 2r. This fragment was cloned into the vector pGEM-T easy vector and sequenced, making it possible to confirm that the oligonucleotide primers used are indeed in the same reading frame. This nucleotide fragment was used as a probe for screening a *Streptomyces noursei* genomic DNA library, prepared in the cosmid pWED1.

Construction of a *Streptomyces noursei* genomic DNA library:

The genomic DNA (2.5 µg), extracted from *Streptomyces noursei* according to standard procedures (Kieser et al., mentioned above; J. Sambrook et al., Molecular cloning: a laboratory manual. Cold Spring Harbor Laboratory Press. Cold Spring Harbor, N.Y. (1989)) was partially digested with 0.33 U of BamHI, resulting in DNA fragments of approximately 35 to 45 kb. These fragments are introduced by ligation into the cosmid vector pWED1 digested with BamHI and dephosphorylated beforehand. The ligation product was encapsulated in vitro in lambda phages (Packagene Lambda DNA packaging system, Promega) and introduced by transfection into the *E. coli* (SURE) strain.

Screening of the *Streptomyces noursei* genomic DNA library:

The nucleotide fragment amplified by RT-PCR was then labeled by random priming with [α-$^{32}$P]-dCTP using the T7 Quick Prime kit (Pharmacia), and used as a probe for screening the library. Approximately 2000 clones were tested by colony hybridization according to the standard method (J. Sambrook et al., mentioned above) and 12 clones were selected. The corresponding cosmids (referred to as pSL110 to pSL121) were extracted, digested with BamHI and analyzed by the Southern blotting technique using the RT-PCR fragments as a probe. This probe made it possible to isolate a 3.8 kb nucleotide fragment common to all the cosmids and also present in the *Streptomyces noursei* genomic DNA digested with BamHI. This BamHI fragment was isolated from the cosmid pSL117 and cloned into the vector pBC SK$^+$, to give the vector pSL122 (definition of the vectors used: cf. table II).

EXAMPLE 2

Analysis of the Sequence of the Polynucleotide of the Invention

The automatic sequencing of the polynucleotides of the invention was carried out on an ABI PRISM Genetic Analyzer (Perkin Elmer) using the DYEnamic ET terminator cycle kit (Pharmacia) or by the company Genome Express. Computer analysis of the sequences and comparisons with the databanks were carried out with the Frame (Bibb, M. J. et al., Gene, 30, 157–166 (1984)), BLAST and FASTA (Altschul, S. F. et al., Nucleic Acids Res., 25, 3389–3402 (1997); Pearson, W. R., Methods in Enzymology, 183, 63–98 (1990)) programs.

Figure 1:
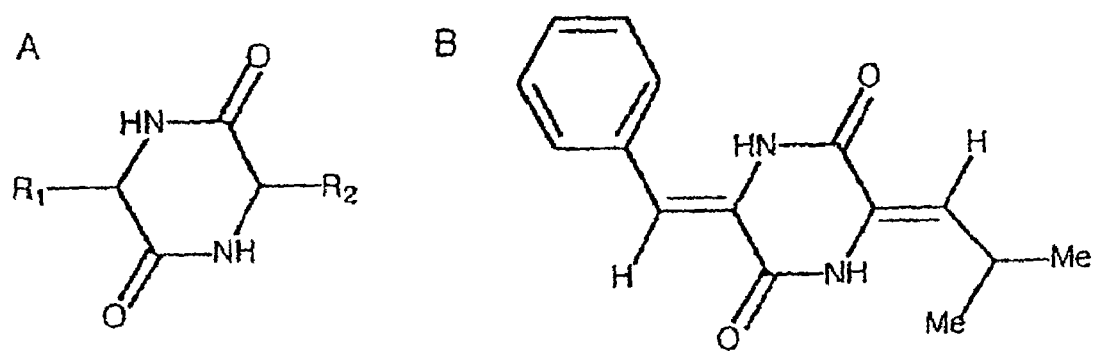
FIG. 1 represents the chemical structures of a diketopiperazine ring (A) and of albonoursin (B).
Figure 2:
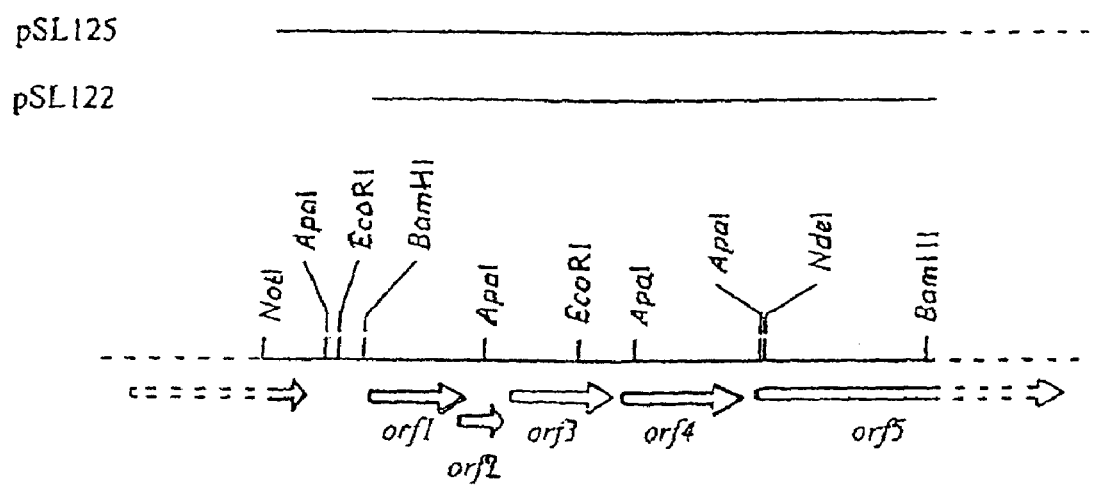
FIG. 2 represents a diagram of the genomic region of *Streptomyces noursei* including the gene cluster required for the synthesis of albonoursin, in which orf1 corresponds to albA, orf2 corresponds to albB, orf3 corresponds to albC, and orf4 corresponds to albD.
Figure 3:
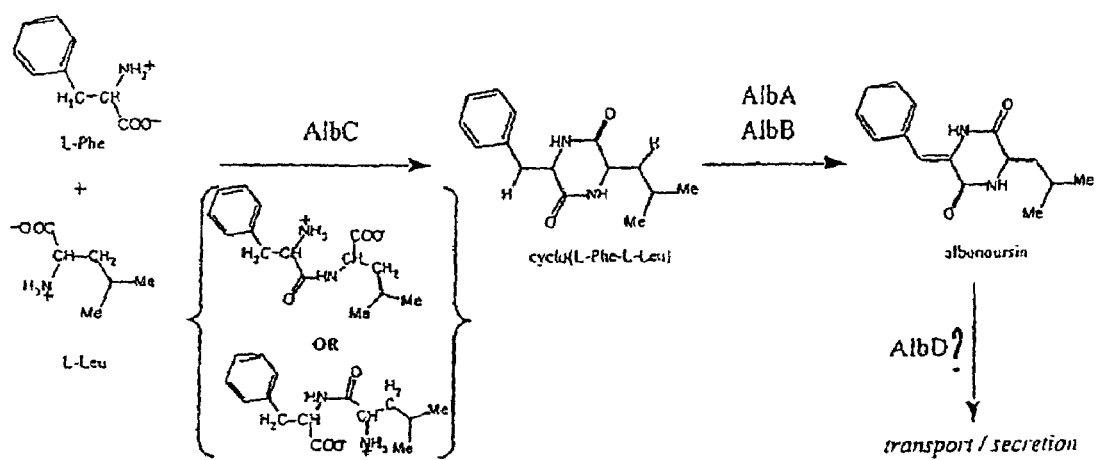
FIG. 3 represents the presumed synthetic pathway for albonoursin *Streptomyces noursei*.

Analysis of the BamHI polynucleotide (SEQ ID No.5) by means of the FRAME program reveals four complete open reading frames, referred to as orf1 to orf4 (albA to albD, SEQ ID Nos.1 to 4) transcribed in the same direction, and an open reading frame (1119 bp) the end of which is truncated, referred to as orf5 (see FIG. 2). The orf5 translation product exhibits a very high degree of similarity with the N-terminal portion of an NADP-specific glutamate dehydrogenase from *Streptomyces coelicolor* (78% identity and 86% similarity according to the BLAST program).

The first of the open reading frames, orf1 (albA, SEQ ID No.1), contains the nucleotide sequence of the fragment amplified by RT-PCR, and the deduced peptide sequence indeed contains the sequence of the 3 trypsin peptides initially isolated. The product of orf1 corresponds, consequently, to the enzymatic protein of approximately 21 kDa in mass, isolated and purified from *Streptomyces noursei* (M. Gondry et al., mentioned above). Consequently, this gene is clearly involved in the biosynthesis of albonoursin and will be referred to as albA.

Analysis of the sequence of albA (orf1) indicates that 3 codons, two GUGs and one AUG, could be considered as initiation codons for the translation of albA, which would result in proteins of 219, 204 or 196 amino acids. Since attempts to determine the N-terminal peptide sequence failed, due to the presence of a post-translational modification on this end, the longest sequence (657 nucleotides) was selected for albA (SEQ ID No.6) (the first initiation codon is located at a distance of 20 nucleotides from the end of the BamHI fragment which, consequently, does not contain the promoter region which must be located further upstream of this gene).

Comparison of the peptide sequence deduced from albA (AlbA, SEQ ID No.6) with the databases showed a maximum degree of similarity with an NADH oxidase from *Archaeoglobus fulgidus* (32% identity and 52% similarity according to the BLAST program) and the search for conserved domains indicates that it has a large nitroreductase-type domain (pfam00881, 151 amino acids).

Orf2 (albB, SEQ ID No.2), which is contiguous with albA, but with a reading frame shift, also exhibits typical *Streptomyces* codon use. albB is translated as two isoforms (AlbB$_1$, SEQ ID No.7 and AlbB$_2$, SEQ ID No.8) that are required for the activity of the AlbA polypeptide, according to the initiation codon AUG or GUG, taken into consideration for orf2. The two isoforms of AlbB, which are expressed in reasonably equivalent amount, differ by virtue of the presence of 5 additional amino acids located at the N-terminal end of AlbB$_1$ and that result from the use of two different initiation codons. In the case of AlbB$_1$, the initial methionine is eliminated.

The two possibilities are compatible with the analysis of the sequence using the FRAME program. The BLAST and FASTA programs reveal no particular homology between the peptide sequence deduced from orf2 and the proteins of the databanks.

Similarly, searches in the databanks carried out based on the polypeptide sequences deduced, respectively, from orf3 (albC, SEQ ID No.3) and orf4 (albD, SEQ ID No.4) reveal no significant homology with a protein of known function. orf3 begins with an ATG initiation codon and encodes a polypeptide of 239 amino acids, AlbC (SEQ ID No.9), which exhibits a low degree of similarity with two hypothetical proteins of unknown function: Rv2275 from *Mycobacterium tuberculosis* (34% identity and 53% similarity according to the BLAST program) and YvmC from *Bacillus subtilis* (29% identity and 46% similarity according to BLAST). Orf4 encodes a 277 amino acid protein, AlbD (SEQ ID No.10), which comprises a transmembrane domain, as indicated by the analysis of its sequence with the TMHMM program (Krogh, A. et al., J. Mol. Biol. 305, (2001)), and exhibits a weak homology with a transmembrane protein of unknown function from *Streptomyces coelicolor* (54% identity and 67% similarity according to BLAST).

EXAMPLE 3

Cloning of the Polynucleotides albA, albB, albC and albD and Construction of the Expression Vectors The methods for extraction and preparation of DNA, for transformation of the *Escherichia coli* and *Streptomyces lividans* TK 21 strains, and for preparation of the protoplasts were carried out according to the standard protocols described by Sambrook et al. (mentioned above) and Kieser et al. (mentioned above).

Figure 4:
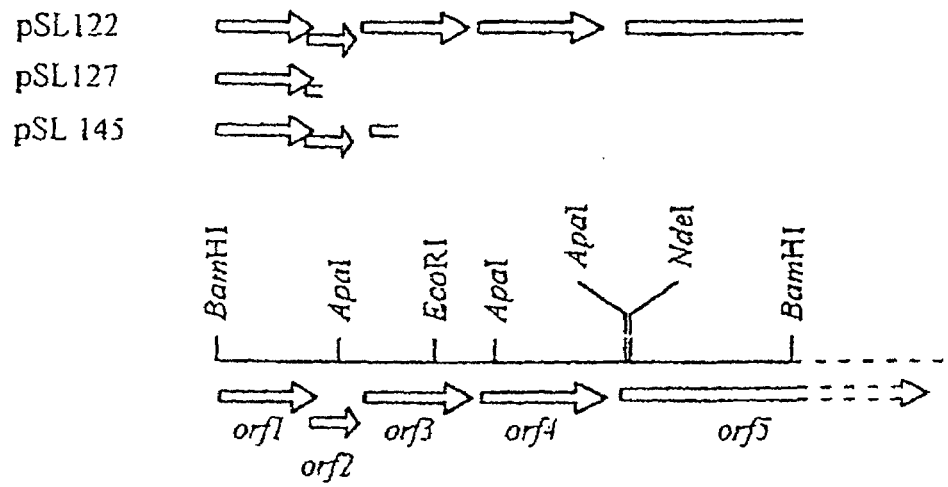
FIG. 4 represents certain plasmid constructs prepared in order to introduce the various open reading frames (or orfs) into *Escherichia coli* or *Streptomyces lividans*.
Figure 4:
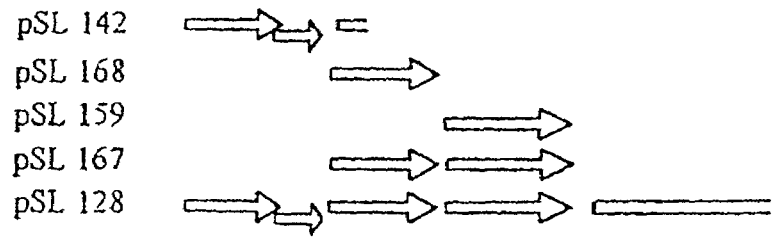

All the plasmid and cosmid vectors prepared for manipulating the polynucleotides which are the subject of the present invention are given in table II (see also FIG. 4).

TABLE II

Strains and vectors used

|  | Properties | Source/reference |
|---|---|---|
| Bacteria | | |
| E. coli DH5α | standard strain for cloning | Invitrogen |
| E. coli SURE | strain used for cosmid libraries | Stratagene |
| Streptomyces lividans TK21 | Streptomyces strain for cloning the alb genes | Hopwood, D. A. et al. J. Gen. Microbol. 129, 2257–2269 (1983). |
| Streptomyces noursei ATCC 1145 | wild-type strain producing albonoursin | ATCC |
| Vectors | | |
| pGEM-T easy | Vector for cloning the PCR products, $Amp^R$ | Promega |
| pWED1 | Cosmid vector derived from pWE15, $Amp^R$ | Gourmelen, A. et al., Antimicrobial Agents Chemotherapy, 42, 2612–2619 (1998) |
| pBC SK+ | Cloning vector, $Cm^R$ | Stratagene |
| pHP45 Ωaac | Plasmid used at source for the cassette Ωaac, $Amp^R$, $Apr^R$ | Blondelet-Rouault, M. H. et al., Gene, 190, 315–317 (1997). |
| pUWL201 | E. coli/Streptomyces shuttle vector, contains the ErmeE* promoter for the expression of cloned genes in Streptomyces. $Amp^R$, $Thio^R$ | Doumith, M., et al., Mol. Gen. Genet. 264, 477–485 (2000) |
| pET-28a | Expression vector | Novagen |
| pSL117 | Cosmids from the Streptomyces noursei library, used for the RT-PCR products | |
| pSL122 | 3.8 kb BamHI fragment cloned into pBC SK+ | |
| pSL127 | pSL122 derivative, comprising an internal deletion of the ApaI fragment, eliminating orf2, orf3, orf4 and orf5 | |
| pSL128 | 3.8 kb BamHI fragment of pSL122, cloned into pUWL201, under the control of Erme*p | |
| pSL129 | 3.8 kb BamHI fragment of pSL122, cloned into pUWL201, containing the insertion in the opposite direction to pSL128 | |
| pSL138 | pSL122 derivative, comprising an internal deletion of the EcoRI fragment, eliminating orf3, orf4 and orf5, and with insertion of the Ωaac cassette | |
| pSL140 | Psl122 derivative, comprising an internal deletion of the NdeI/EcoRV fragment eliminating orf5, and with the insertion of the Ωaac cassette | |
| pSL142 | Asp718/Klenow/BamHI fragment of pSL138 (containing orf1, orf2 and the Ωaac cassette) cloned into pUWL201 | |
| pSL144 | Asp718/Klenow/BamHI fragment of pSL140 (containing orf1 to orf4 and the Ωaac cassette) cloned into pUWL201 | |
| pSL145 | pSL122 derivative with internal deletion of the EcoRI fragment, eliminating orf3, orf4 and orf5 | |
| pSL150 | PCR product from amplification of orf1–orf2, cloned into the expression vector pET-28a | |
| pSL157 | PCR product from amplification of orf4, cloned into pGEM-T easy | |

TABLE II-continued

Strains and vectors used

| | Properties | Source/reference |
|---|---|---|
| pSL159 | PstI/Klenow/BamHI fragment of pSL157 cloned into pUWL201 | |
| pSL165 | PCR product from amplification of orf3, cloned into pGEM-T easy | |
| pSL166 | PCR product from amplification of orf3 + orf4, cloned into pGEM-T easy | |
| pSL167 | PstI/Klenow/BamHI fragment of pSL166 cloned into pUWL201 | |
| pSL168 | PstI/Klenow/BamHI fragment of pSL165 cloned into pUWL201 | | pSL117 is a cosmid containing the *Streptomyces noursei* genomic DNA library.

pSL122 contains the 3.8 kb BamHI polynucleotide (SEQ ID No.5) from *Streptomyces noursei* which is the subject of the invention, cloned into the cloning vector pBC SK+. pSL127 and pSL145 were constructed, respectively, by digestion of pSL122 with ApaI or EcoRI, and religation.

The BamHI polynucleotide was also cloned into the *E. coli/Streptomyces* shuttle vector pUWL201, in the orientation appropriate for having all the genes under the control of the ermE* promoter (pSL128) or else in the opposite orientation (pSL129).

pSL142 and pSL144 were constructed in 2 steps: pSL122 was first digested with EcoRI and the Klenow enzyme, or NdeI and the Klenow enzyme, and then a ligation between these fragments and the Ωaac cassette digested with HindIII-Klenow resulted in the plasmids pSL138 and pSL140. These plasmids were then digested with Asp718, Klenow and BamHI, and the fragments obtained containing orf1 (albA, SEQ ID No.1), orf2 (albB, SEQ ID No.2) and the Ωaac cassette, for the first, and orf1 to orf4 (albA to albD) and the Ωaac cassette, for the second, are cloned into the vector pUWL201 digested with XbaI-Klenow-BamHI.

orf3 (albC, SEQ ID No.3), orf4 (albD, SEQ ID No.4) and (orf3+orf4) were amplified by PCR using the following primers:

for orf3

```
sylv24:
                                        (SEQ ID N°20)
5'-CGGCTGCAGGAGAAGGGAGCGGACATATGCTTGCAGGCTTAGTTCC
C-3':,
(PstI site underlined);

sylv22:
                                        (SEQ ID N°21)
5'-CGGTCCCGTGGATCCAAGCTTCTAGGCCGCGTCGGCCAGCTC-3':,
(BamHI site underlined);

for orf4 sylv19:
                                        (SEQ ID N°22)
5'-GAGCGGGATCCTGCAGTGTCATGGGGAGGACAGGAC-3':,
(PstI site underlined);

sylv18:
                                        (SEQ ID N°23)
5'-CGATCACGTGGATCCAAGCTTGGCAATCCTGTACGCGATTT-3':,
(BamHI site underlined);

for (orf3 + orf4):sylv24 and sylv18.
``` orf2 and orf3 are separated only by 37 nucleotides, a synthetic ribosome-binding site was included in sylv24 in order to ensure correct translation of orf3. The fragments amplified by PCR were then cloned into the vector pGEM-T easy (Promega), to give pSL165, pSL157 and pSL166. The PstI-BamHI fragments obtained from these three plasmids were then cloned into the vector pUWL201 digested with PstI-BamHI, to give pSL168, pSL159 and pSL167.

EXAMPLE 4

Production of the Diketopiperazine Derivative Cyclo(ΔPhe-ΔLeu) (Albonoursin) in a Heterologous Host, *Streptomyces lividans*, Transformed by Introduction of the BamHI Polynucleotide (SEQ ID No.5)

*Streptomyces lividans* TK21 protoplasts were transformed with pSL128 (containing the BamHI polynucleotide (SEQ ID No.5)), pSL129 or pUWL201 (control) according to the standard protocols described by Sambrook et al. (mentioned above) and Kieser et al. (mentioned above). The three strains were cultured in M5 medium (ATCC medium), a rich medium containing a large excess of amino acids, for 3 days at a temperature of between 28 and 30° C. The supernatants from the cultures of the 3 transformed strains were analyzed by reverse-phase HPLC under the following conditions: the culture supernatant (500 µl) was filtered (ultrafree-MC 10 kDa, Millipore) and injected directly onto HPLC (Vydac C18 column (4.6×250 mm): flow rate: 1 ml/min; elution: linear gradient of 0 to 45% of acetonitrile in 0.1% of trifluoroacetic acid in 45 minutes). The elution was monitored using a multi-wavelength detector for between 200 and 600 nm.

Figure 5:
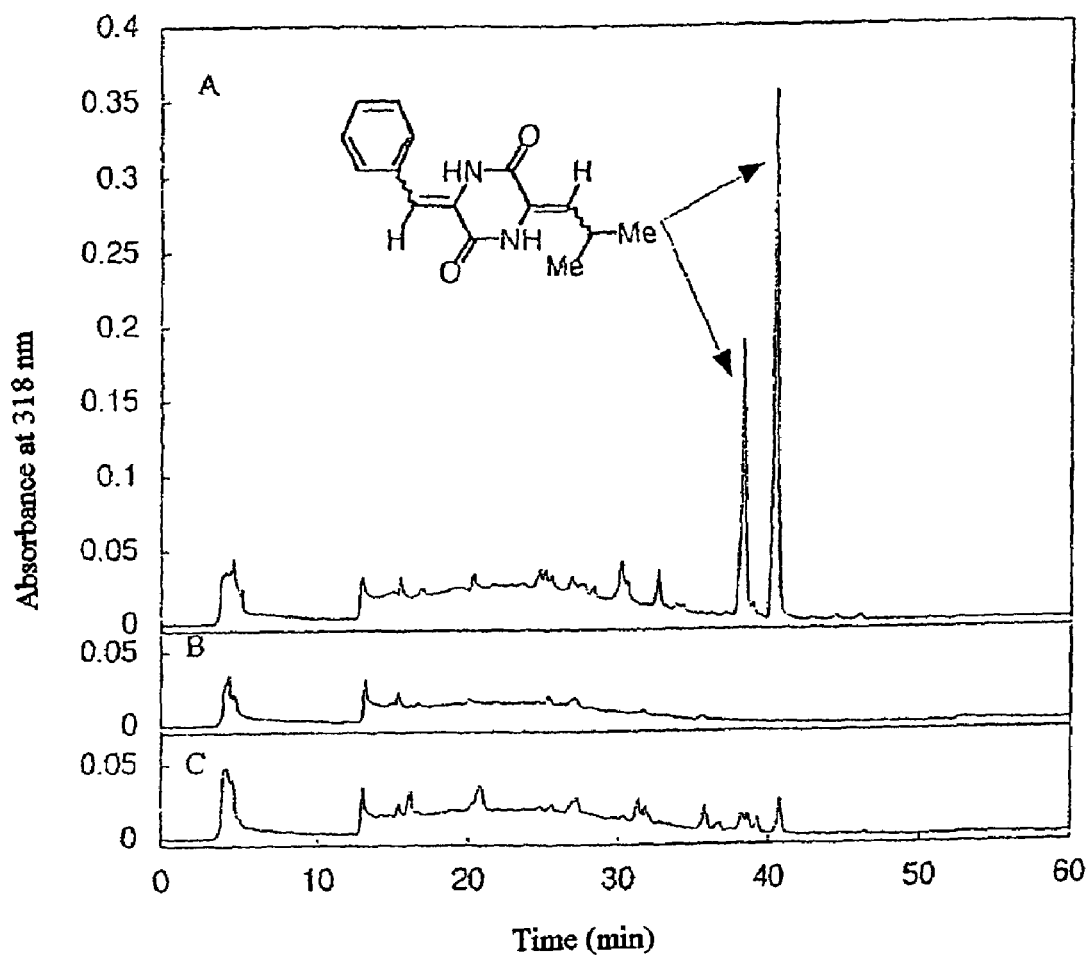
FIG. 5 represents the results of the analyses of the culture media for *Streptomyces lividans*, transformed by introduction of the plasmids pSL128(A), pUWL201 (B) and pSL129 (C).

The production of albonoursin in 2 stereoisomeric forms (2 peaks at 38.3 min and 40.5 min; $\lambda_{max}$=318 nm; m=256.4 Da) is detected in *S. lividans*[pSL128] (FIG. 5A).

In the control strains *S. lividans*[pUWL201] and *S. lividans*[pSL129] (FIGS. 5B and 5C), no production of albonoursin is detected.

The BamHI polynucleotide (SEQ ID No.5) from *Streptomyces noursei* contains all the genetic information for the production of albonoursin.

EXAMPLE 5

Demonstration of the Function of the Poly-Nucleotides albA and albB by Visualization of the Conversion of Cyclo(L-Trp-L-Trp) to Cyclo(ΔTrp-ΔTrp) in a Petri Dish Using a Heterologous Host, *Escherichia coli*, Transformed by Insertion of the Polynucleotides albA and albB A rapid test in a Petri dish was developed in order to directly detect the conversion of cyclodipeptides to bisdehydro cyclodipeptides on isolated colonies. This test is based on the conversion of the cyclodipeptide, which is colorless in solution, cyclo(L-Trp-L-Trp), to a yellow and insoluble product, cyclo(ΔTrp-ΔTrp) ($\lambda_{max}$=367 nm and 450 nm), which gives the colonies exhibiting the CDO activity a bright yellow color.

The *E. coli* strains transformed with the plasmids prepared according to the protocol explained in detail in example 3 were tested directly on a dish of LB medium containing 0.5 mM of cyclo{L-Trp-L-Trp}.

After incubation for 16 hours at 37° C., the *E. coli* [pSL122] (containing the BamHI polynucleotide) and *E. coli*[pSL145] (containing the BamHI fragment with a deletion of orf3 to orf5) strains exhibit a strong yellow coloration, whereas *E. coli*[pBC SK+] (containing the intact cloning vector) and *E. coli*[pSL127] (containing the BamHI fragment with a deletion of orf2 to orf5) are not colored.

This result demonstrates the involvement of the two genes orf1 (albA, SEQ ID No.1) and orf2 (albB, SEQ ID No.2) in the cyclodipeptide oxidase activity associated with the production of albonoursin.

EXAMPLE 6

Expression of the Cyclodipeptide Oxidase (CDO) Enzyme Activity in a Heterologous Host, *Streptomyces lividans*, Transformed by Introduction of orf1 and orf2 (albA and albB, SEQ ID No.1 and SEQ ID No.2)

The HPLC analysis of the supernatant from culturing the *Streptomyces lividans* TK21 strain transformed with the plasmid pSL142 containing the BamHI polynucleotide from which orf3 (albC, SEQ ID No.3), orf4 (albD, SEQ ID No.4) and orf5 have been deleted, under the culture conditions described in example 4, demonstrate an absence of production of albonoursin and therefore indicates the involvement of orf3 and/or orf4 in the production of the diketopiperazine derivative.

However, the addition of cyclo(L-Phe-L-Leu) to the supernatant, under the standard conditions described in Gondry et al. (mentioned above), clearly results in the production of albonoursin. This suggests the involvement of orf3 and/or orf4 in the biosynthesis of the cyclodipeptide cyclo(L-Phe-L-Leu).

EXAMPLE 7

Demonstration of the Production of Cyclo(L-Phe-L-Leu) and Cyclo(L-Phe-L-Phe) in vivo in a Heterologous Host, *Streptomyces lividans*, Transformed by Introduction of orf3 (albC, SEQ ID No.3)

In order to confirm the results described in example 6, orf3 (albC) and orf4 (albD) were cloned separately into the shuttle plasmid pUWL201, giving, respectively, pSL168 (orf3) and pSL159 (orf4), which were introduced into *Streptomyces lividans* TK21 according to the standard protocols described by Sambrook et al. (mentioned above) and Kieser et al. (mentioned above).

After culturing under the conditions described in example 4, the *S. lividans* [pSL168] and *S. lividans* [pSL159] culture supernatants were analyzed by HPLC, under the standard conditions described in example 4, in order to demonstrate the production of the cyclodipeptide cyclo(L-Phe-L-Leu). Since direct detection of this compound is difficult due to its low molar adsorption coefficient ($\epsilon_{mol}\approx$100 M$^{-1}$cm$^{-1}$ at 254 nm) and to the complexity of the medium, the demonstration thereof was carried out after conversion of the cyclodipeptide to albonoursin (cyclo(ΔPhe-ΔLeu), $\epsilon_{mol}$=25120 M$^{-1}$.cm$^{-1}$ at 318 nm), by addition of the CDO enzyme purified according to the method described in Gondry et al. (mentioned above).

The culture supernatants were filtered, and then incubated for 10 to 15 hours at 30° C. with 4.1×10$^{-3}$ enzyme units of purified CDO. Compared HPLC analysis of the culture supernatants, incubated or not incubated with CDO, was performed. The molecular mass of the metabolites produced was determined by mass spectrometry (Quattro II, Micromass).

Figure 6:
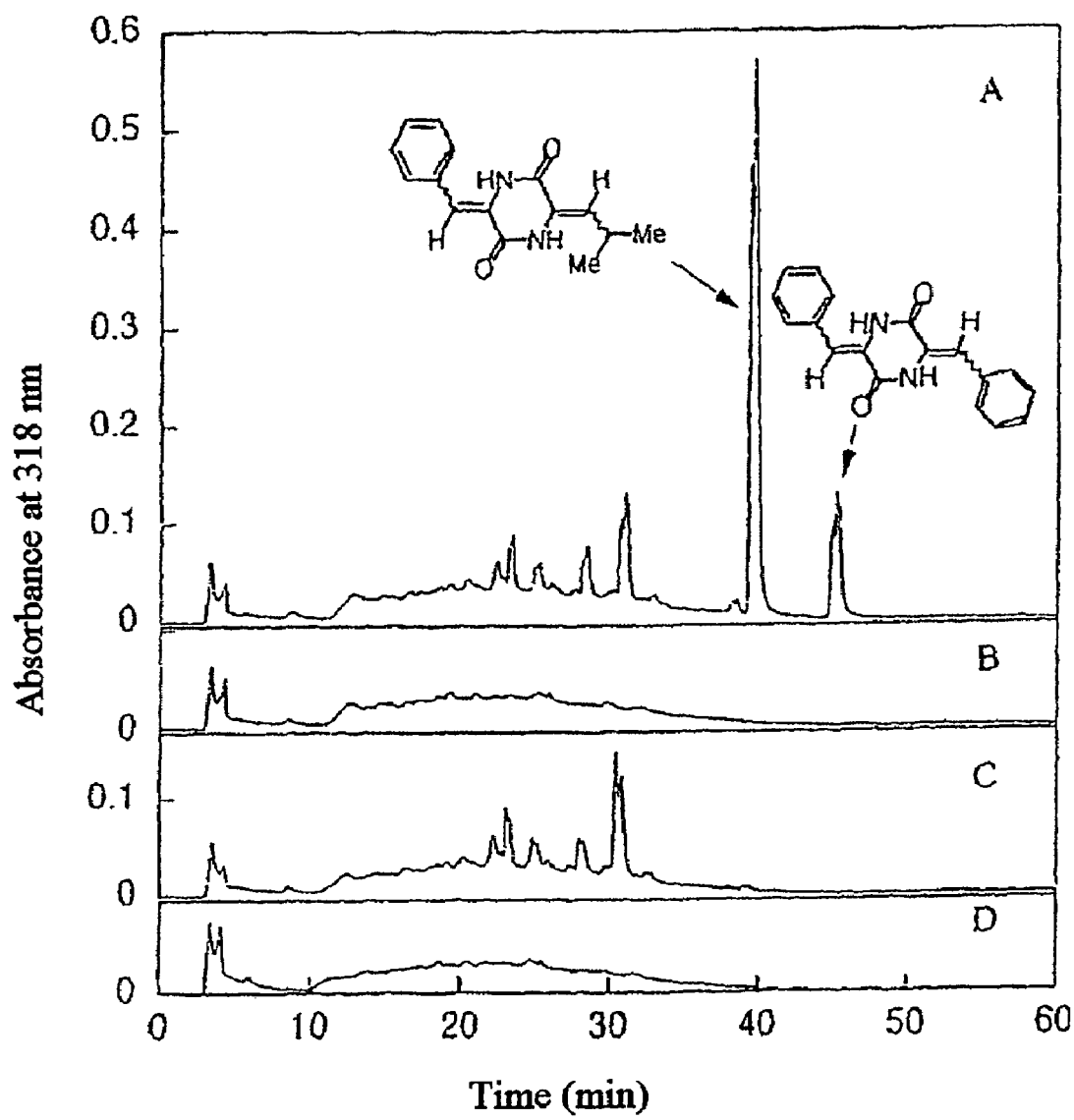
FIG. 6 represents the results of the analyses of the culture media for *Streptomyces lividans*, transformed by introduction of the plasmids pSL168 and pSL159, or for nontransformed *Streptomyces lividans*.

The results are given in FIG. 6:

In the culture supernatant from *S. lividans*[pSL168], incubated in the presence of CDO, albonoursin (cyclo(ΔPhe-ΔLeu)) (peak at 40.5 min; $\lambda_{max}$=318 nm; m=256.4 Da) and cyclo(ΔPhe-ΔPhe) (peak at 44.1 min; $\lambda_{max}$=338 nm; m=290.3) (panel A) are detected;

No metabolite is detected:
in the culture supernatant from *S. lividans*[psL168] in the absence of CDO (panel B);
in the culture supernatant from *S. lividans*[pSL159] in the absence or in the presence of CDO (panel C);
in the culture supernatant from *Streptomyces lividans* TK21 incubated in the presence of CDO: (panel D).

This result clearly demonstrates the involvement of orf3 (albC) in the production of the cyclodipeptides cyclo(L-Phe-L-Leu), the precursor for albonoursin, and cyclo(1-Phe-L-Phe), the precursor for a second metabolite, cyclo(ΔPhe-ΔPhe), produced together initially in *Streptomyces noursei* (Khokhlov A. S. et al., Tetrahedron Lett., 27; 1881 (1963)).

EXAMPLE 8

Demonstration of the Production of Cyclo-(L-Phe-L-Leu) and Cyclo(L-Phe-L-Phe) in vivo in a Heterologous Host, *Streptomyces lividans*, Transformed by Introduction of the Polynucleotide orf3–orf4 (albC–albD, SEQ ID No.3–SEQ ID No.4).

According to a variation of example 7, the polynucleotide orf3–orf4 (albC-albD) was cloned into the shuttle plasmid pUWL201, and the resulting plasmid, pSL167, was introduced into *Streptomyces lividans* TK21 according to the standard protocols described by Sambrook et al. (mentioned above) and Kieser et al. (mentioned above).

HPLC analysis of the culture supernatant, treated in an identical manner to the method described in example 7, shows that, in the culture supernatant from *S. lividans* [pSL167] incubated in the presence of CDO, albonoursine (cyclo(ΔPhe-ΔLeu)) and cyclo(ΔPhe-ΔPhe) are detected and that no metabolite is detected in the culture supernatant from *S. lividans*[pSL167] in the absence of CDO, nor in the culture supernatant from *Streptomyces lividans* TK21 incubated in the presence of CDO.

These results demonstrate that the product of the orf5 gene does not participate directly in the biosynthesis of albonoursine, whereas ofr4, (albC), is necessary and sufficient to produce the precursor cyclo-dipeptides cyclo(L-Phe-L-Leu) and cyclo(L-Phe-L-Phe), in *Streptomyces lividans* as in *Streptomyces noursei*.

EXAMPLE 9

Overexpression of AlbA and AlbB from the Polynucleotide albA–albB (SEQ ID No.1–SEQ ID No.2)

The vector pET-28a(+), which contains an N-terminal or C-terminal polyhistidine sequence (His tag), was used to construct an expression vector containing the polynucleotide albA–albB, in order to facilitate the purification of the recombinant protein. The shortest sequence of albA, encoding a polypeptide of 196 amino acid residues, was chosen. The gene amplification of the polynucleotide by PCR was carried out using oligonucleotide primers designed so as to include an NdeI (sense) and XhoI (antisense) cloning site.

The PCR conditions are as follows: initial denaturation at 94° C. for 4 min, followed by 10 cycles of 1 minute at 94° C., 1 minute at 45° C. and 1.5 minutes at 72° C., and then by 20 cycles of 1 minute at 94° C., 1 minute at 50° C. and 1.5 minutes at 72° C., and a final polymerization reaction at 72° C. for 10 min. The reaction products were digested with NdeI and XhoI, and the fragments were subcloned into the vector pET-28a, to give pSL150. The sequence of the insert was verified by automatic sequencing (ABI PRISM Genetic analyzer, Perkin Elmer) using the DYEnamic ET terminator cycle kit (Amersham Pharmacia Biotech).

Standard expression conditions were used:
growth temperature: 20° C.,
induction of expression: 0.6 mM IPTG
induction time: 16 hours.

pSL150 was introduced into *E. coli* BL21 (DE3)-plysS. The strain was cultured in LB medium at 20° C. until an absorbence of 0.6 was obtained, and then expression was induced. The culture was then centrifuged at 4190 g, at 4° C. for 15 min. The cells were then resuspended in extraction buffer (100 mM Tris-HCl, pH 8.0, 1 µM phosphoramidon, 1 mM PMSF and 5% glycerol), and ground with an Eaton press. The protein extract was incubated in the presence of benzonase (25 U/ml) at 30° C. for 10 min, and then centrifuged at 11300 g for 15 min at 4° C. The enzyme activity was determined according to the standard assay described by Gondry et al. (mentioned above). One unit of enzyme activity is defined as the amount of enzyme that catalyzes the production of 1 µmol of product per minute, and the specific activity is expressed in units of enzyme per mg of proteins. The specific activity of the enzyme extract was increased by a factor of 50 (As=2 U/mg) after purification of affinity chromatography (column: HiTrap chelating HP (1 ml), Amersham Pharmacia Biotech; equilibration of $Ni^{2+}$ ions in 100 mM Tris-HCl buffer, pH 8.0, containing 0.5 M NaCl and 10 mM imidazole; elution: gradient of 0.3 to 1 M imidazole in 35 min; flow rate: 1 ml/min).

The sodium dodecyl sulfate/polyacrylamide gel (SDS-PAGE) (12%) analysis of the purified fraction of *E. coli* [pSL150] (FIG. 7) demonstrates the simultaneous presence of AlbA and AlbB in non-stoichiometric proportions, and demonstrates that AlbB is expressed as 2 isoforms (2 bands in SDS-PAGE). The analysis of purified AlbB by mass spectrometry and N-terminal sequencing of the polypeptide sequence indicates that these two forms correspond to the products $AlbB_1$ and $AlbB_2$ from the 2 initiation codons identified in its sequence (cf. above).

EXAMPLE 10

In vitro Conversion of Cyclo(L-Phe-L-His) and Cyclo(L-Phe-L-Leu) by Recombinant AlbA–AlbB The enzyme preparation purified according to the method described in example 9, incubated under the standard conditions as described by Gondry et al. (mentioned above), catalyzes the in vitro conversion of cyclopeptides to monodehydro and bisdehydro cyclo-dipeptides.

The purified enzyme preparation was incubated in the presence of the cyclo(L-Phe-L-His) substrates for 72 h at 30° C. The reaction products were analyzed by reverse-phase HPLC under the conditions described in example 4, and identified on the basis of their spectral characteristics and of their molecular mass confirmed by mass spectrometry. The reaction products are as follows:

from cyclo(L-Phe-L-His): cyclo(ΔPhe-L-His) at ($\lambda_{max}$=297 nm and m=282 Da) and cyclo(ΔPhe-Δ-His) ($\lambda_{max}$=338 nm and m=280 Da), from cyclo(L-Phe-L-Leu): cyclo(ΔPhe-L-Leu) ($\lambda_{max}$=297 nm and m=258 Da) and cyclo(ΔPhe-Δ-Leu) ($\lambda_{max}$=316 nm and m=256 Da).

These results confirm that the enzyme preparation obtained from cloning the polynucleotide albA–albB into an expression vector introduced into a heterologous host catalyzes in vitro, the conversion of cyclo-dipeptides to α,β-dehydrogenated diketopiperazine derivatives.

---

What is claimed is:

1. An isolated polynucleotide comprising the open reading frame of SEQ ID No.3.

2. A vector, comprising the polynucleotide as claims 1.

3. The vector as claimed in claim 2, characterized in that it is a plasmid, a cosmid, a bacterial artificial chromosome (BAC), an integrative element of actinobacteria, a virus or a bacteriophage.

4. An isolated polypolypeptide characterized in that it comprises SEQ ID No.9.

5. An isolated polypeptide characterized in that it is encoded by the polynucleotide as claimed in claim 1 or a vector comprising said polynucleotide.

6. A method for producing a polypeptide, comprising expresssing the polynucleotide of claim 1 or a vector comprising said polynucleotide under effective conditions.

7. A method for prenaring a biological system, comprising transfecting the polynucleotide of claim 1 or of a vector comprising said polynucleotide into a microorganism, and allowing the expression of the polynucleotid.

8. A method for expressing a polynucleotide, comprising transfecting the polynucleotide of claim 1 or a vector comprising said polynucleotide into an isolated heterologous host cell selected from prokaryotic or eukaryotic cells, and allowing the expression of the polynucleotide.

9. An isolated biological system, comprising the polynucleotide as described in claim 1 or at least one vector comprising said polynucleotide.

10. The biological system as claimed in claim 9, further comprising a microorganism, a heterologous expression system comprising an isolated host cell selected from a prokaryotic or eukaryotic host cell, or a cell-free translation system.

11. The biological system as claimed in claim 10, characterized in that the microorganism is a bacterium selected from *Escherichia coli* or *Streptomyces lividans*.

12. A cell free translation system, comprising the polynucleotide of claim 1 or a vector comprising said polynucleotide.

* * * * *

UNITED STATES PATENT AND TRADEMARK OFFICE
CERTIFICATE OF CORRECTION

PATENT NO. : 7,112,425 B2
APPLICATION NO. : 10/518019
DATED : September 26, 2006
INVENTOR(S) : Gondry et al.

It is certified that error appears in the above-identified patent and that said Letters Patent is hereby corrected as shown below:

Claim 2, Column 37, Line 4,
Please delete
"claims" and replace with -- claim --

Claim 7, Column 37, Line 17,
Please delete
"prenaring" and replace with -- preparing --

Claim 7, Column 37, Line 20,
Please delete
"polynucleotid" and replace with
-- polynucleotide --

Signed and Sealed this

Second Day of January, 2007

JON W. DUDAS
*Director of the United States Patent and Trademark Office*

SEQUENCE LISTING

<160> NUMBER OF SEQ ID NOS: 23

<210> SEQ ID NO 1
<211> LENGTH: 657
<212> TYPE: DNA
<213> ORGANISM: Streptomyces noursei

<400> SEQUENCE: 1

```
gtgaggcgcc acccatcgca ttcgccgtac cgcggcgggt gtgaggtgcg cccaaaaaga      60
aggggattga tgttagctca cagttcatct gaatcgccgc cggaatcctt gccggacgcg     120
```

-continued

```
tggacggtcc tcaaaacccg taccgccgtc cgcaattacg cgaaagagcc ggtcgacgac    180
gcgctgatcg agcagctgtt ggaggccatg ctcgccgcgc cgaccgcctc caaccggcag    240
gcgtggtcgt tcatggtggt gcgcaggccc gccgcggtcc gccggctgcg cgcgttctcg    300
cccggggtgc tgggaacccc cgccttcttc gtcgtggcct cgtcgaccg cagtctgacc     360
gacaacctct ccccgaagct ctcgcagaag atctacgaca ccagcaagct ctgtgtcgcc    420
atggcggtgg agaacctgct gctcgcggcg cacgcggccg gcctgggcgg atgcccggtg    480
ggcagcttca ggtccgacat cgtcaccagc atgctcggta tcccggaaca catcgagccg    540
atgctcgtgg tcccgatcgg ccgtcccgcg acagccctcg tccctccca gcgccgcgcc     600
aagaatgagg tcgtcaacta tgaatcctgg ggaaaccgtg ctgccgcccc aactgcg      657
```

<210> SEQ ID NO 2
<211> LENGTH: 318
<212> TYPE: DNA
<213> ORGANISM: Streptomyces noursei

<400> SEQUENCE: 2

```
atgaatcctg gggaaaccgt gctgccgccc caactgcgtg aggagatcgc gctcctcgcc    60
gtctatctgc tcagcagcgg ccgcggactc ctggaggagc cggccgacta cggaatttac    120
cgctgtaccg acggggcccg tcgggcgctc caactcctcg acgaacacgg cgggagcacg    180
gcacggctga ccgccgtccg cgagcgtctc gacgaggtca tgttcgcgcc gatgggcgag    240
gaccgggaca tgggcgcgat tctggacgac ctgtgtcgcc aaatggcaga cgctcttccg    300
gaaattgaaa ccccctga                                                 318
```

<210> SEQ ID NO 3
<211> LENGTH: 720
<212> TYPE: DNA
<213> ORGANISM: Streptomyces noursei

<400> SEQUENCE: 3

```
atgcttgcag gcttagttcc cgcgccggac cacggaatgc gggaagaaat acttggcgac    60
cgcagccgat tgatccggca acgcggtgag cacgccctca tcggaatcag tgcgggcaac    120
agttatttca gccagaagaa caccgtcatg ctgctgcaat gggccgggca gcgtttcgag    180
cgcaccgatg tcgtctatgt cgacacccac atcgacgaga tgctgatcgc cgacggccgc    240
agcgcgcagg aggccgagcg gtcggtcaaa cgcacgctca aggatctgcg gcgcagactc    300
cggcgctcgc tggagagcgt gggcgaccac gccgagcggt tccgtgtccg gtccctgtcc    360
gagctccagg agacccctga gtaccgggcc gtacgcgagc gcaccgaccg ggccttcgag    420
gaggacgccg aattcgccac cgcctgcgag gacatggtgc gggccgtggt gatgaaccgg    480
cccggtgacg gcgtcggcat ctccgcggaa cacctgcggg ccggtctgaa ctacgtgctg    540
gccgaggccc cgctcttcgc ggactcgccc ggagtcttct ccgtcccctc ctcggtgctc    600
tgctaccaca tcgacacccc gatcacggcg ttcctgtccc ggcgcgagac cggtttccgg    660
gcggccgagg gacaggcgta cgtcgtcgtc aggccccagg agctggccga cgcggcctag    720
```

<210> SEQ ID NO 4
<211> LENGTH: 834
<212> TYPE: DNA
<213> ORGANISM: Streptomyces noursei -continued

```
<400> SEQUENCE: 4
atgtcatggg gaggacagga cacttgctca tggtgcggaa cggggcccct cggcgaagct      60
gaagacgtag gaagacagca cacgtcgcac gccgggggac ccgtcatgac tcaagccgcc     120
accgtcaccg ccaccacgag ccagggcagg gcactcctgc ggagcctgac gccgctgttc     180
gtggacgccg cgatcccgct cggctcgtac ttcctcctcg ccgagggctt cggcatgagc     240
acggtcgccg cgctggcctg gagcagcgtg gtcccgcgcg tgcgcacgat ctggggcctg     300
gtccgggagc ggacggtcaa cggcctcgcg ctgctgatcc tcgtcgtcaa cgtggtgggg     360
ctggcgacga gcaccctgac cggcgatgcc cggctgatga tggccaagga cagcggcgtc     420
agcagcgtcg tcgggatcgc gatcctgctc tcggtgcgcg gccggcgccc gctgatgacc     480
gccggactcc ggccctgggt gaccaaggga agcccggagg ggaacgccgc atgggaccgg     540
ctgtgggcgc gcagcgcgcg gttccggcaa ctggagcggc gattctcgac ggtctggggg     600
agcgccctgc tgatcgagtg cgtggtcaag gtcgtcggtg cgtacgtcct gccggtgcac     660
accatggtgt ggctgggcac ggtgctgacg gtggtggcga tcctgctggc catggtggtc     720
gcgggcggcg gcagcgccga gccgatggag cggatggtca aggccgaggt cggggccgcc     780
ggcgaggccg ccacggcggg gaacgccgag ccggcgccgg ccgccgcggc ctga           834

<210> SEQ ID NO 5
<211> LENGTH: 3839
<212> TYPE: DNA
<213> ORGANISM: Streptomyces noursei

<400> SEQUENCE: 5
ggatccgtcc cgacgggcgg gaaccggtga ggcgccaccc atcgcattcg ccgtaccgcg      60
gcgggtgtga ggtgcgccca aaaagaaggg gattgatgtt agctcacagt tcatctgaat     120
cgccgccgga atccttgccg gacgcgtgga cggtcctcaa aacccgtacc gccgtccgca     180
attacgcgaa agagccggtc gacgacgcgc tgatcgagca gctgttggag gccatgctcg     240
ccgcgccgac cgcctccaac cggcaggcgt ggtcgttcat ggtggtgcgc aggcccgccg     300
cggtccgccg gctgcgcgcg ttctcgcccg gggtgctggg aaccccgcc ttcttcgtcg      360 tggcctgcgt cgaccgcagt ctgaccgaca acctctcccc gaagctctcg cagaagatct     420
acgacaccag caagctctgt gtcgccatgg cggtggagaa cctgctgctc gcggcgcacg     480
cggccggcct gggcggatgc ccggtgggca gcttcaggtc cgacatcgtc accagcatgc     540
tcggtatccc ggaacacatc gagccgatgc tcgtggtccc gatcggccgt cccgcgacag     600
ccctcgtccc ctcccagcgc cgcgccaaga atgaggtcgt caactatgaa tcctggggaa     660
accgtgctgc cgccccaact gcgtgaggag atcgcgctcc tcgccgtcta tctgctcagc     720
agcggccgcg gactcctgga ggagccggcc gactacggaa tttaccgctg taccgacggg     780
gcccgtcggg cgctccaact cctcgacgaa cacggcggga gcacggcacg gctgaccgcc     840
gtccgcgagc gtctcgacga ggtcatgttc gcgccgatgg gcgaggaccg ggacatgggc     900
gcgattctgg acgacctgtg tcgccaaatg gcagacgctc ttccggaaat tgaaccccc      960 tgacggctgt ccggggcaac cccaaaagga cttcttagca tgcttgcagg cttagttccc    1020
gcgccggacc acgaatgcg ggaagaaata cttggcgacc gcagccgatt gatccggcaa     1080
cgcggtgagc acgccctcat cggaatcagt gcgggcaaca gttatttcag ccagaagaac    1140
accgtcatgc tgctgcaatg ggccgggcag cgtttcgagc gcaccgatgt cgtctatgtc    1200
gacacccaca tcgacgagat gctgatcgcc gacgccgca gcgcgcagga ggccgagcgg     1260
```

-continued

```
tcggtcaaac gcacgctcaa ggatctgcgg cgcagactcc ggcgctcgct ggagagcgtg    1320
ggcgaccacg ccgagcggtt ccgtgtccgg tccctgtccg agctccagga gaccctgag     1380 taccgggccg tacgcgagcg caccgaccgg gccttcgagg aggacgccga attcgccacc    1440
gcctgcgagg acatggtgcg ggccgtggtg atgaaccggc ccgtgacgg cgtcggcatc     1500 tccgcggaac acctgcgggc cggtctgaac tacgtgctgg ccgaggcccc gctcttcgcg    1560
gactcgcccg gagtcttctc cgtcccctcc tcggtgctct gctaccacat cgacaccccg    1620
atcacggcgt tcctgtcccg gcgcgagacc ggtttccggg cggccgaggg acaggcgtac    1680
gtcgtcgtca ggcccagga gctggccgac gcggcctagt tggggcgtc cgcgggcgga      1740 cctgcctccc cacccgctcc cggtgccggc gccgggcatg acaaatgtca tggggaggac    1800
aggacacttg ctcatggtgc ggaacggggc ccctcggcga agctgaagac gtaggaagac    1860
agcacacgtc gcacgccggg ggacccgtca tgactcaagc cgccaccgtc accgccacca    1920
cgagccaggg cagggcactc ctgcggagcc tgacgccgct gttcgtggac gccgcgatcc    1980
cgctcggctc gtacttcctc ctcgccgagg gcttcggcat gagcacggtc gccgcgctgg    2040
cctggagcag cgtggtcccg gcgctgcgca cgatctgggg cctggtccgg gagcggacgg    2100
tcaacggcct cgcgctgctg atcctcgtcg tcaacgtggt ggggctggcg acgagcaccc    2160
tgaccggcga tgcccggctg atgatggcca aggacagcgg cgtcagcagc gtcgtcggga    2220
tcgcgatcct gctctcggtg cgcggccggc gcccgctgat gaccgccgga ctccggcccct   2280 gggtgaccaa gggaagcccg gaggggaacg ccgcatggga ccggctgtgg gcgcgcagcg    2340
cgcggttccg gcaactggag cggcgattct cgacggtctg ggggagcgcc ctgctgatcg    2400
agtgcgtggt caaggtcgtc ggtgcgtacg tcctgccggt gcacaccatg gtgtggctgg    2460
gcacggtgct gacggtggtg gcgatcctgc tggccatggt ggtcgcgggc ggcggcagcg    2520
ccgagccgat ggagcggatg gtcaaggccg aggtcgggc cgccggcgag ccgccacgg      2580 cggggaacgc cgagccggcg ccggccgccg cggcctgaga ccgcgcggcg ggggagttgg    2640
ggaaatcgcg tacaggattg gcgcgtcgag caccccgcc ctcgataggg cgggcccccg     2700
gcgcatatgg tcggcgatgc gacgggacat cggagccccg cgtcgacggt tcaacggcga    2760
tccggacggc acgcgctttt cgtcggccac gaagggaacg gaagtcatgt cgactgttca    2820
cactggggtc acgcagagcg gtctcaccgc cgagctggcc tccctgcacg ccgagctcgt    2880
ccgtcggaat cccggtgaag cggagttcca ccaggcggcc ctggaggtcc tcgaaacgct    2940
ggcaccggtg ctcaccgccc ggccggagtt cgccgacgcc aaggtcctgg agcggatcgt    3000
cgagccggag cggcagatca tgttccgcgt gccctggcag gacgactccg gcacgatccg    3060
ggtcaaccgc ggcttccggg tggagttcaa cagcgcgctc ggcccctaca agggcggcct    3120
gcggttccac gcgtccgtca acctcggcat cgtgaagttc ctcggcttcg agcagatctt    3180
caagaacgcc ctgaccgggc tgaacatcgg cggcggcaag ggcggcagcg acttcgaccc    3240
gcacggcagg tcggacgccg aggtgatgcg cttctgccag tccttcatga ccgagctgca    3300
ccgtcacctg ggcgagcaca ccgacgtgcc ggctggcgac atcggcgtcg gcggccggga    3360
gatcggctac ctcttcggcc agtaccggcg gatcaccaac cgctgggagg ccggcgtcct    3420
gaccggcaag ggcctggcgt ggggcggctc caaggcccgt acggaggcca ccggttacgg    3480
caatgtgctg ttcaccgagg agatgctcaa gcagcgcggc gaggagctgg acggccagca    3540
ggtggtggtc tccgggtccg gcaacgtcgc catctacacc atcgagaagg cccaggcgct    3600
cggcgccaac gtcctgaccg tctcggactc cggcggctac gtcgtcgacg agaagggcat    3660
```

-continued

```
cgacctggcg ctgctcaagc aggtcaagga ggtcgagcgc ggccgggtcg gcgactacgc    3720
ccagcggcgc ggcagttcgg cgaagtacgt cgccggcggg agcgtgtggg acgtcgcctg    3780
tgacgtggcg ctgccgtcgg ccacccagaa cgagctcgac gcggacgccg cccggatcc     3839
```

<210> SEQ ID NO 6
<211> LENGTH: 219
<212> TYPE: PRT
<213> ORGANISM: Streptomyces noursei

<400> SEQUENCE: 6

```
Met Arg Arg His Pro Ser His Ser Pro Tyr Arg Gly Gly Cys Glu Val
  1               5                  10                  15

Arg Pro Lys Arg Arg Gly Leu Met Leu Ala His Ser Ser Glu Ser
             20                  25                  30

Pro Pro Glu Ser Leu Pro Asp Ala Trp Thr Val Leu Lys Thr Arg Thr
         35                  40                  45

Ala Val Arg Asn Tyr Ala Lys Glu Pro Val Asp Asp Ala Leu Ile Glu
     50                  55                  60

Gln Leu Leu Glu Ala Met Leu Ala Ala Pro Thr Ala Ser Asn Arg Gln
 65                  70                  75                  80

Ala Trp Ser Phe Met Val Val Arg Pro Ala Ala Val Arg Arg Leu
                 85                  90                  95

Arg Ala Phe Ser Pro Gly Val Leu Gly Thr Pro Ala Phe Phe Val Val
            100                 105                 110

Ala Cys Val Asp Arg Ser Leu Thr Asp Asn Leu Ser Pro Lys Leu Ser
        115                 120                 125

Gln Lys Ile Tyr Asp Thr Ser Lys Leu Cys Val Ala Met Ala Val Glu
    130                 135                 140

Asn Leu Leu Leu Ala Ala His Ala Ala Gly Leu Gly Gly Cys Pro Val
145                 150                 155                 160

Gly Ser Phe Arg Ser Asp Ile Val Thr Ser Met Leu Gly Ile Pro Glu
                165                 170                 175

His Ile Glu Pro Met Leu Val Val Pro Ile Gly Arg Pro Ala Thr Ala
            180                 185                 190

Leu Val Pro Ser Gln Arg Arg Ala Lys Asn Glu Val Val Asn Tyr Glu
        195                 200                 205

Ser Trp Gly Asn Arg Ala Ala Ala Pro Thr Ala
    210                 215
```

<210> SEQ ID NO 7
<211> LENGTH: 104
<212> TYPE: PRT
<213> ORGANISM: Streptomyces noursei

<400> SEQUENCE: 7

```
Asn Pro Gly Glu Thr Val Leu Pro Pro Gln Leu Arg Glu Glu Ile Ala
  1               5                  10                  15

Leu Leu Ala Val Tyr Leu Leu Ser Ser Gly Arg Gly Leu Leu Glu Glu
             20                  25                  30

Pro Ala Asp Tyr Gly Ile Tyr Arg Cys Thr Asp Gly Ala Arg Arg Ala
         35                  40                  45

Leu Gln Leu Leu Asp Glu His Gly Gly Ser Thr Ala Arg Leu Thr Ala
     50                  55                  60

Val Arg Glu Arg Leu Asp Glu Val Met Phe Ala Pro Met Gly Glu Asp
 65                  70                  75                  80
```

-continued

```
Arg Asp Met Gly Ala Ile Leu Asp Asp Leu Cys Arg Gln Met Ala Asp
                85                  90                  95

Ala Leu Pro Glu Ile Glu Thr Pro
            100

<210> SEQ ID NO 8
<211> LENGTH: 99
<212> TYPE: PRT
<213> ORGANISM: Streptomyces noursei

<400> SEQUENCE: 8

Met Leu Pro Pro Gln Leu Arg Glu Glu Ile Ala Leu Leu Ala Val Tyr
1               5                   10                  15

Leu Leu Ser Ser Gly Arg Gly Leu Leu Glu Pro Ala Asp Tyr Gly
            20                  25                  30

Ile Tyr Arg Cys Thr Asp Gly Ala Arg Arg Ala Leu Gln Leu Leu Asp
            35                  40                  45

Glu His Gly Gly Ser Thr Ala Arg Leu Thr Ala Val Arg Glu Arg Leu
    50                  55                  60

Asp Glu Val Met Phe Ala Pro Met Gly Glu Asp Arg Asp Met Gly Ala
65                  70                  75                  80

Ile Leu Asp Asp Leu Cys Arg Gln Met Ala Asp Ala Leu Pro Glu Ile
                85                  90                  95

Glu Thr Pro

<210> SEQ ID NO 9
<211> LENGTH: 239
<212> TYPE: PRT
<213> ORGANISM: Streptomyces noursei

<400> SEQUENCE: 9

Met Leu Ala Gly Leu Val Pro Ala Pro Asp His Gly Met Arg Glu Glu
1               5                   10                  15

Ile Leu Gly Asp Arg Ser Arg Leu Ile Arg Gln Arg Gly Glu His Ala
            20                  25                  30

Leu Ile Gly Ile Ser Ala Gly Asn Ser Tyr Phe Ser Gln Lys Asn Thr
        35                  40                  45

Val Met Leu Leu Gln Trp Ala Gly Gln Arg Phe Glu Arg Thr Asp Val
    50                  55                  60

Val Tyr Val Asp Thr His Ile Asp Glu Met Leu Ile Ala Asp Gly Arg
65                  70                  75                  80

Ser Ala Gln Glu Ala Glu Arg Ser Val Lys Arg Thr Leu Lys Asp Leu
                85                  90                  95

Arg Arg Arg Leu Arg Arg Ser Leu Glu Ser Val Gly Asp His Ala Glu
            100                 105                 110

Arg Phe Arg Val Arg Ser Leu Ser Glu Leu Gln Glu Thr Pro Glu Tyr
        115                 120                 125

Arg Ala Val Arg Glu Arg Thr Asp Arg Ala Phe Glu Glu Asp Ala Glu
    130                 135                 140

Phe Ala Thr Ala Cys Glu Asp Met Val Arg Ala Val Met Asn Arg
145                 150                 155                 160

Pro Gly Asp Gly Val Gly Ile Ser Ala Glu His Leu Arg Ala Gly Leu
                165                 170                 175

Asn Tyr Val Leu Ala Glu Ala Pro Leu Phe Ala Asp Ser Pro Gly Val
            180                 185                 190
```

```
Phe Ser Val Pro Ser Ser Val Leu Cys Tyr His Ile Asp Thr Pro Ile
        195                 200                 205

Thr Ala Phe Leu Ser Arg Arg Glu Thr Gly Phe Arg Ala Ala Glu Gly
        210                 215                 220

Gln Ala Tyr Val Val Arg Pro Gln Glu Leu Ala Asp Ala Ala
225                 230                 235

<210> SEQ ID NO 10
<211> LENGTH: 277
<212> TYPE: PRT
<213> ORGANISM: Streptomyces noursei

<400> SEQUENCE: 10

Met Ser Trp Gly Gly Gln Asp Thr Cys Ser Trp Cys Gly Thr Gly Pro
1               5                   10                  15

Leu Gly Glu Ala Glu Asp Val Gly Arg Gln His Thr Ser His Ala Gly
            20                  25                  30

Gly Pro Val Met Thr Gln Ala Ala Thr Val Thr Ala Thr Thr Ser Gln
        35                  40                  45

Gly Arg Ala Leu Leu Arg Ser Leu Thr Pro Leu Phe Val Asp Ala Ala
    50                  55                  60

Ile Pro Leu Gly Ser Tyr Phe Leu Leu Ala Glu Gly Phe Gly Met Ser
65                  70                  75                  80

Thr Val Ala Ala Leu Ala Trp Ser Ser Val Pro Ala Leu Arg Thr
                85                  90                  95

Ile Trp Gly Leu Val Arg Glu Arg Thr Val Asn Gly Leu Ala Leu Leu
            100                 105                 110

Ile Leu Val Val Asn Val Val Gly Leu Ala Thr Ser Thr Leu Thr Gly
        115                 120                 125

Asp Ala Arg Leu Met Met Ala Lys Asp Ser Gly Val Ser Ser Val Val
    130                 135                 140

Gly Ile Ala Ile Leu Leu Ser Val Arg Gly Arg Arg Pro Leu Met Thr
145                 150                 155                 160

Ala Gly Leu Arg Pro Trp Val Thr Lys Gly Ser Pro Glu Gly Asn Ala
                165                 170                 175

Ala Trp Asp Arg Leu Trp Ala Arg Ser Ala Arg Phe Arg Gln Leu Glu
            180                 185                 190

Arg Arg Phe Ser Thr Val Trp Gly Ser Ala Leu Leu Ile Glu Cys Val
        195                 200                 205

Val Lys Val Val Gly Ala Tyr Val Leu Pro Val His Thr Met Val Trp
    210                 215                 220

Leu Gly Thr Val Leu Thr Val Val Ala Ile Leu Leu Ala Met Val Val
225                 230                 235                 240

Ala Gly Gly Gly Ser Ala Glu Pro Met Glu Arg Met Val Lys Ala Glu
                245                 250                 255

Val Gly Ala Ala Gly Glu Ala Ala Thr Ala Gly Asn Ala Glu Pro Ala
            260                 265                 270

Pro Ala Ala Ala Ala
        275

<210> SEQ ID NO 11
<211> LENGTH: 20
<212> TYPE: PRT
<213> ORGANISM: Streptomyces noursei
```

<400> SEQUENCE: 11

Glu Pro Val Asp Asp Ala Leu Ile Glu Gln Leu Leu Glu Ala Met Leu
1               5                   10                  15

Ala Ala Pro Thr
            20

<210> SEQ ID NO 12
<211> LENGTH: 12
<212> TYPE: PRT
<213> ORGANISM: Streptomyces noursei
<220> FEATURE:
<221> NAME/KEY: misc_feature
<222> LOCATION: (8)..(8)
<223> OTHER INFORMATION: Xaa can be any naturally occurring amino acid

<400> SEQUENCE: 12

Asn Glu Val Val Asn Tyr Glu Xaa Trp Gly Asn Arg
1               5                   10

<210> SEQ ID NO 13
<211> LENGTH: 9
<212> TYPE: PRT
<213> ORGANISM: Streptomyces noursei
<220> FEATURE:
<221> NAME/KEY: misc_feature
<222> LOCATION: (3)..(3)
<223> OTHER INFORMATION: Xaa can be any naturally occurring amino acid

<400> SEQUENCE: 13

Gln Ala Xaa Ser Phe Met Val Val Arg
1               5

<210> SEQ ID NO 14
<211> LENGTH: 17
<212> TYPE: DNA
<213> ORGANISM: Artificial
<220> FEATURE:
<223> OTHER INFORMATION: primer

<400> SEQUENCE: 14
garccsgtsg acgacgc                                                  17

<210> SEQ ID NO 15
<211> LENGTH: 17
<212> TYPE: DNA
<213> ORGANISM: Artificial
<220> FEATURE:
<223> OTHER INFORMATION: primer

<400> SEQUENCE: 15
gcgtcgtcsa csggytc                                                  17

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
aacgargtsg tsaactacga                                               20

<210> SEQ ID NO 17
<211> LENGTH: 20
<212> TYPE: DNA
<213> ORGANISM: Artificial

```
<220> FEATURE:
<223> OTHER INFORMATION: primer

<400> SEQUENCE: 17
tcgtagttsa csacytcgtt                                              20

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
caggcstggw ssttcatggt                                              20

<210> SEQ ID NO 19
<211> LENGTH: 20
<212> TYPE: DNA
<213> ORGANISM: Artificial
<220> FEATURE:
<223> OTHER INFORMATION: primer

<400> SEQUENCE: 19
accatgaass wccasgcctg                                              20

<210> SEQ ID NO 20
<211> LENGTH: 47
<212> TYPE: DNA
<213> ORGANISM: Artificial
<220> FEATURE:
<223> OTHER INFORMATION: primer

<400> SEQUENCE: 20
cggctgcagg agaagggagc ggacatatgc ttgcaggctt agttccc                47

<210> SEQ ID NO 21
<211> LENGTH: 42
<212> TYPE: DNA
<213> ORGANISM: Artificial
<220> FEATURE:
<223> OTHER INFORMATION: primer

<400> SEQUENCE: 21
cggtcccgtg gatccaagct tctaggccgc gtcggccagc tc                    42

<210> SEQ ID NO 22
<211> LENGTH: 36
<212> TYPE: DNA
<213> ORGANISM: Artificial
<220> FEATURE:
<223> OTHER INFORMATION: primer

<400> SEQUENCE: 22
gagcgggatc ctgcagtgtc atggggagga caggac                            36

<210> SEQ ID NO 23
<211> LENGTH: 41
<212> TYPE: DNA
<213> ORGANISM: Artificial
<220> FEATURE:
<223> OTHER INFORMATION: primer

<400> SEQUENCE: 23
cgatcacgtg gatccaagct tgccaatcct gtacgcgatt t                     41
```